(12) United States Patent
Benner

(10) Patent No.: US 7,544,794 B1
(45) Date of Patent: Jun. 9, 2009

(54) METHOD FOR SEQUENCING DNA AND RNA BY SYNTHESIS

(76) Inventor: Steven Albert Benner, 1501 NW. 68th Terr., Gainesville, FL (US) 32605-4147

( * ) Notice: Subject to any disclaimer, the term of this patent is extended or adjusted under 35 U.S.C. 154(b) by 400 days.

(21) Appl. No.: 11/373,415

(22) Filed: Mar. 11, 2006

Related U.S. Application Data

(60) Provisional application No. 60/661,142, filed on Mar. 11, 2005.

(51) Int. Cl.
   *C07H 19/044* (2006.01)
   *C07H 10/16* (2006.01)
   *C07H 19/167* (2006.01)
   *C07H 19/173* (2006.01)
   *C07H 19/20* (2006.01)

(52) U.S. Cl. .............. 536/27.61; 536/27.62; 536/27.81; 536/28.5; 536/28.53; 536/28.52; 536/28.54; 536/28.1

(58) Field of Classification Search ........................ None
See application file for complete search history.

(56) References Cited

U.S. PATENT DOCUMENTS

| | | | |
|---|---|---|---|
| 5,489,677 A * | 2/1996 | Sanghvi et al. | ............ 536/22.1 |
| 5,610,289 A * | 3/1997 | Cook et al. | |
| 5,623,070 A * | 4/1997 | Cook et al. | |
| 6,232,465 B1 * | 5/2001 | Hiatt et al. | ................ 536/26.26 |
| 6,664,079 B2 * | 12/2003 | Ju et al. | ...................... 435/91.1 |

FOREIGN PATENT DOCUMENTS

WO    WO 94/22454    * 10/1994
WO    WO 94/22886    * 10/1994

OTHER PUBLICATIONS

Hwang et al., "Evidence for Watson-Crick and Not Hoogsteen or Wobble Base Pairing in the Selection of Nucleotides for Insertion Opposite Pyrimidines and a Thymine Dimer by Yeast DNA Pol n" Biochemistry (2005) vol. 44, pp. 4850-4860.*
Burgess et al., "Synthesis of an Oxyamide linked Nucleotide Dimer and Incorporation into Antisense Oligonucleotide Sequences" Journal of the Chemical Society, Chemical Communications (1994) pp. 915-916.*
Patent prosecution documents from U.S. Appl. No. 11/513,916, (a) Office action with a mail date of Apr. 14, 2008, raising a 35 USC 102(b) objection, (b) Reply to the above office action, mailed May 7, 2008, traversing the 35USC 102(b) objection, (c) Office action with a mail date of Mar. 23, 2009, maintaining the 35 USC 102(b) objection, (d) Reply to the above office action, mailed Apr. 29, 2009, again traversing the 35 USC 102(b) objection.*

* cited by examiner

*Primary Examiner*—Shaojia Anna Jiang
*Assistant Examiner*—Eric S Olson

(57) ABSTRACT

This invention relates to the field of nucleic acid chemistry, more specifically to the field of compositions and processes that are nucleic acid analogs. More specifically, this invention relates to compositions that allow the sequencing of oligonucleotides by synthesis, and processes for sequencing by synthesis that exploit these compositions. Most specifically, the instant invention discloses compositions of matter that are 5'-triphosphates of ribo- and 2'-deoxyribonucleosides wherein the 3'-OH group is replaced by a 3'-ONHR group in the alpha configuration, wherein R is either a H or $CH_3$ group. Also disclosed are these triphosphates where the nucleobase carries, via a linker, a reporter groups, such as a fluorescent species that can be used in single- or multi-copy DNA sequencing, or a tag that can be visualized by ultramicroscopy. Also disclosed are processes that use these compositions to do sequencing by synthesis.

6 Claims, 18 Drawing Sheets

Figure 1. Sequencing by synthesis

Figure 6
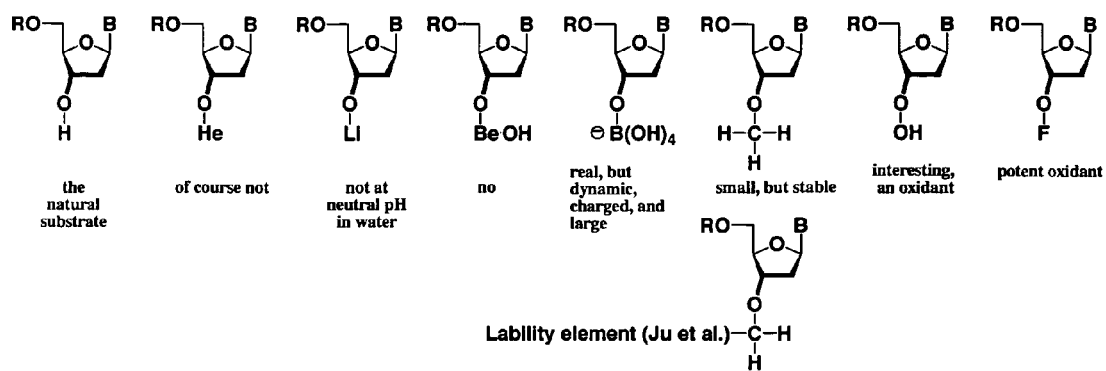
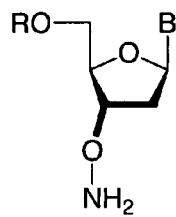

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Synthetic, chemically synthesized

<400> SEQUENCE: 1
tgcctaacga                                                         10

<210> SEQ ID NO 2
<211> LENGTH: 16
<212> TYPE: DNA
<213> ORGANISM: Artificial Sequence
<220> FEATURE:
<223> OTHER INFORMATION: Synthetic, chemically synthesized

<400> SEQUENCE: 2
cagcagtcgt taggca                                                  16
```

METHOD FOR SEQUENCING DNA AND RNA BY SYNTHESIS

This application claims benefit of provisional application 60/661,142, filed Mar. 11, 2005.

FIELD

This invention relates to the field of nucleic acid chemistry, more specifically to the field of compositions and processes that can be used to determine the sequences of nucleic acids. More specifically, this invention relates to compositions that allow the sequencing of oligonucleotides by synthesis.

BACKGROUND

The ability to sequence and re-sequence (a term that describes the sequencing of a new genome while making reference to the genome of a closely related organism, generally of the same species) deoxyribonucleic acid (DNA) has the potential for revolutionizing biology and medicine. The ability to re-sequence segments of the genome of individual humans will enable the personalization of medicine, as the genetic differences between individuals carries information about how those individuals will respond differently to similar treatments [Ros00]. Most DNA sequencing is done today using capillary array DNA sequencers that detect fluorescent dyes appended to the 5- or 7-positions of pyrimidine or 7-deazapurine nucleobases attached to dideoxynucleotide analogs [Smi86][Ju95][Ju96][Khe96][Sal98]. These analogs, present as a fraction of the total nucleotide triphosphates, irreversibly terminate a growing DNA chain. Mutant polymerases have improved the uniformity and efficiency of termination, improving the quality of sequencing data [Tab87][Tab95].

While these strategies have created the post-genomic world, they have well known limitations. Primary among them is that they are difficult to multiplex, and a difficulty to do sequencing on small numbers of molecules, including sequencing on single molecules.

In part to enhance multiplexing, in part for other reasons, sequencing by synthesis without using electrophoresis was introduced as a strategy in 1988 [Hym88]. This approach involves detecting the identity of each nucleotide as it is incorporated into the growing strand of DNA in a polymerase-catalyzed reaction. Such a strategy, coupled with the chip format and laser-induced fluorescent detection, was proposed to have the potential of increasing the throughput of DNA sequencing, largely due to multiplexed sequencing. These approaches are referred to herein as "sequencing by synthesis", even though the term is somewhat inappropriate. Synthesis is, of course, involved in classical DNA sequencing, meaning that these approaches are perhaps better denoted as sequencing with analysis concurrent with synthesis.

A variety of architectures have been proposed for sequencing by synthesis [Che94] [Met94]. The pyrosequencing architecture employs four natural nucleotides (comprising a base of adenine (A), cytosine (C), guanine (G), or thymine (T)) and several other enzymes for sequencing DNA by synthesis [Ron98]. In this architecture, detection is based on the release of pyrophosphate during the DNA polymerase reaction. This is converted to adenosine triphosphate (ATP) by sulfurylase, which then generates visible light in the presence of firefly luciferase. The limitations of this procedure are also well known in the art. Each of the four nucleotides must be added and detected separately. The procedure is not likely to ever be able to sequence long runs.

Another architecture has a polymerase direct the incorporation, in a template-directed polymerization step, of a nucleoside triphosphate or thiotriphosphate (which is useful in certain architectures) having its 3'-hydroxyl group blocked by a removable protecting (or capping) group, which carries one of four tags, distinctive for the four nucleobases. fluorescent group. Then, after the blocked nucleotide is incorporated and the nature of the nucleotide incorporated is determined by reading the tag, the 3'-protecting group is removed to generate a 3'-OH group at the 3'-end of the elongating primer. This permits the next cycle of sequencing to occur.

In this architecture, template-directed polymerization is done using a DNA polymerase or, conceivably, a reverse transcriptase [Mit03]. The identity of each nucleotide is determined as it is incorporated. The most common proposal to do this requires that incorporated nucleotide carry a fluorescent tag. When the output is fluorescence, the strategy requires:

(a) Four analogues of dATP, dTTP, dGTP, and dCTP, that each carry a fluorescent dye with a different color, with the 3'-end blocked so that elongation is not possible.

(b) The four analogues must be efficiently incorporated, to permit the elongation reaction to be completed before undesired reactions occur, and to avoid ragged ends arising from incomplete incorporation. For single molecule sequencing, this is less critical, but still undesirable, as a cycle of sequence collection is missed.

(c) The incorporation must be faithful. Mismatched incorporation, if not corrected by proofreading, will lead to the loss of strands if the polymerase does not extend efficiently a terminal mismatch. This will gradually erode the intensity of the signal, and may generate "out of phase" signals that confuse the reading of the output downstream. Large numbers of errors will, of course, confuse the primary signal. For single molecule sequencing, misincorporation may well mean the end of a read.

(d) The dye and the group capping the 3'-OH group need to be removed with high yield to allow the incorporation of the next nucleotide of the next nucleotide to proceed. Less than 99% completion for each cycle (and incompletion) will gradually erode the intensity of the signal, and may generate "out of phase" signals that confuse the reading of the output downstream. For single molecule sequencing, failure to cleave the 3'-OH blocking group may not create a decisive error, but it can lose a cycle of sequence data collection.

(e) The growing strand of DNA should survive the washing, detecting and cleaving processes. While reannealing is possible, we preferably would like conditions that allow the DNA primer and template to remain annealed.

It their most ambitious forms, sequencing-by-synthesis architectures were proposed that used the same nucleoside modification to block the 3'-end of the DNA and to introduce the fluorescent tag [Wel99]. The chemistry of this architecture is simple to envision. For example, if the fluorescent tag is attached to the 3'-position via an ester linkage, extension following incorporation would not be possible (there is no free 3'-OH group). This would give time to read the color of the fluorescent label, determining the nature of the nucleotide added. Then, the 3'-O acyl group could be removed by treatment with a mild nucleophile (such as hydroxylamine) under mild conditions (pH<10) to regenerate a free 3'-hydroxyl group, preparing the DNA for the next cycle.

The difficulty in implementing this elegant approach is the polymerases themselves. Crystal structures of polymerases show that the 3'-position in the deoxyribose unit is close to amino acid residues in the active site of the polymerase. The structure of the ternary complexes of rat DNA polymerase beta, a DNA template-primer, and dideoxycytidine triphosphate (ddCTP) from the Kraut laboratory, as well as a variety of structures for other polymerases from other sources solved in other laboratories, illustrates this fact. The polymerase, therefore, is not likely to be able to handle large substituents at the 3'-position. For example, to accept even 2'.3.-dideoxynucleoside analogues, where the substituents at this position is smaller, mutated polymerases are often beneficial.

Ju et al, in U.S. Pat. No. 6,664,079 noted these problems as they outlined a proposal for sequencing by synthesis based on 3'-OH blocking groups. They suggested that this problem might be addressed using nucleotide analogues where the tag, such as a fluorescent dye or a mass tag, is linked through a cleavable linker to the nucleotide base or an analogue of the nucleotide base, such as to the 5-position of the pyrimidines (T and C) and to the 7-position of the purines (G and A). Bulky substituents are known to be accepted at this position; indeed, these are the sites that carry the tags in classical dideoxy sequencing. Tags at this position should, in principle, allow the 3'-OH group to be blocked by a cleavable moiety that is small enough to be accepted by DNA polymerases. In this architecture, cleavage steps would be required to remove both the tag (to make the system clean for the addition of the next tag) and the 3'-blocking group, to permit the next cycle of extension to occur [Mit03][Seo04].

U.S. Pat. No. 6,664,079 then struggled to find a small chemical group that might be accepted by polymerases, and could be removed under conditions that were not so harsh as to destroy the DNA being sequences. U.S. Pat. No. 6,664,079 cited a literature report that 3'-O-methoxy-deoxynucleotides are good substrates for several polymerases [Axe78]. It noted, correctly, that the conditions for removing a 3'-O methyl group were too stringent to permit this blocking group from being removed under any conditions that were likely to leave the DNA being sequenced intact.

An ester group was also discussed as a way to cap the 3'-OH group of the nucleotide. U.S. Pat. No. 6,664,079 discarded this capping group based on a report that esters are cleaved in the active site in DNA polymerase [Can95]. It should be noted that to this report is questionable, and considers only a single polymerase. Therefore, the instant disclosure teaches that is possible that a formyl group could be used in this architecture. 3'-O formylated 2'-deoxynucleoside triphosphates are preparable as intermediates in the Ludwig-Eckstein triphosphate synthesis, if the 3'-O acetyl group that is traditionally used is replaced by a formyl group, and the final alkaline deprotection step is omitted.

Chemical groups with electrophiles such as ketone groups were also considered and discarded by U.S. Pat. No. 6,664,079, as not being suitable for protecting the 3'-OH of the nucleotide in enzymatic reactions due to the existence of strong nucleophiles (such as amino groups) in the polymerase. It should be noted that the 3'-keto 2'-deoxyribose unit is not stable to decomposition via beta elimination reactions, as is well known in the literature studying the mechanism of ribonucleotide reductases.

U.S. Pat. No. 6,664,079 then cited a literature report that 3'-O-allyl-dATP is incorporated by Vent (exo-) DNA polymerase in the growing strand of DNA [Met94]. U.S. Pat. No. 6,664,079 noted that this group, and the methoxymethyl MOM group, having a similar size, might be used to cap the 3'-OH group in a sequencing-by-synthesis format. This patent noted that these groups can be cleaved chemically using transition metal reagents [Ire86][Kam99].

These suggestions therefore define the invention disclosed in U.S. Pat. No. 6,664,079. Briefly, the essence of this invention is an architecture where the triphosphates of four nucleotide analogues, each labeled with a unique cleavable tag attached to the nucleobase, and each having the 3'-OH unit capped with an allyl group (the MOM group not having high utility in this context), are used as the extension groups in the sequencing by synthesis strategy.

This architecture, to date, has never been reduced to practice to give a practical process for sequencing DNA by synthesis. This is again because of the polymerases. While the allyl group is small, to date, no polymerases have been shown to incorporate these to the extent and with the efficiency needed to effectively reduce this invention to practice. Therefore, U.S. Pat. No. 6,664,079 cannot be said to have enabled the sequencing-by-synthesis strategy.

BRIEF DESCRIPTION OF THE DRAWINGS

FIG. 6. A systematic survey of the periodic table shows that the $NH_2$ group is the smallest reversible blocking group that is likely to meet the specs needed for sequencing by synthesis.

DETAILED DESCRIPTION OF THE INVENTION

Various details of the state of the art in the area of sequencing-by-synthesis caused us to re-think the approach. We first considered the size of the 3'-cap in light of the crystal structures of various polymerases. Both the MOM and allyl groups, although small, are still too large to fit comfortably into the active site based on crystallographic analysis (see [Eva00] and papers cited therein). These groups each contain three heavy atoms, defined here to be non-hydrogen atoms, in addition to the 3'-oxygen being protected.

The essence of the instant invention is that a 3'-blocking group that has fewer than three heavy atoms is required for an efficient sequencing by synthesis architecture, either with natural polymerases or with polymerases in which one of the amino acids in contact with the ribose ring is mutated.

Figure 1:
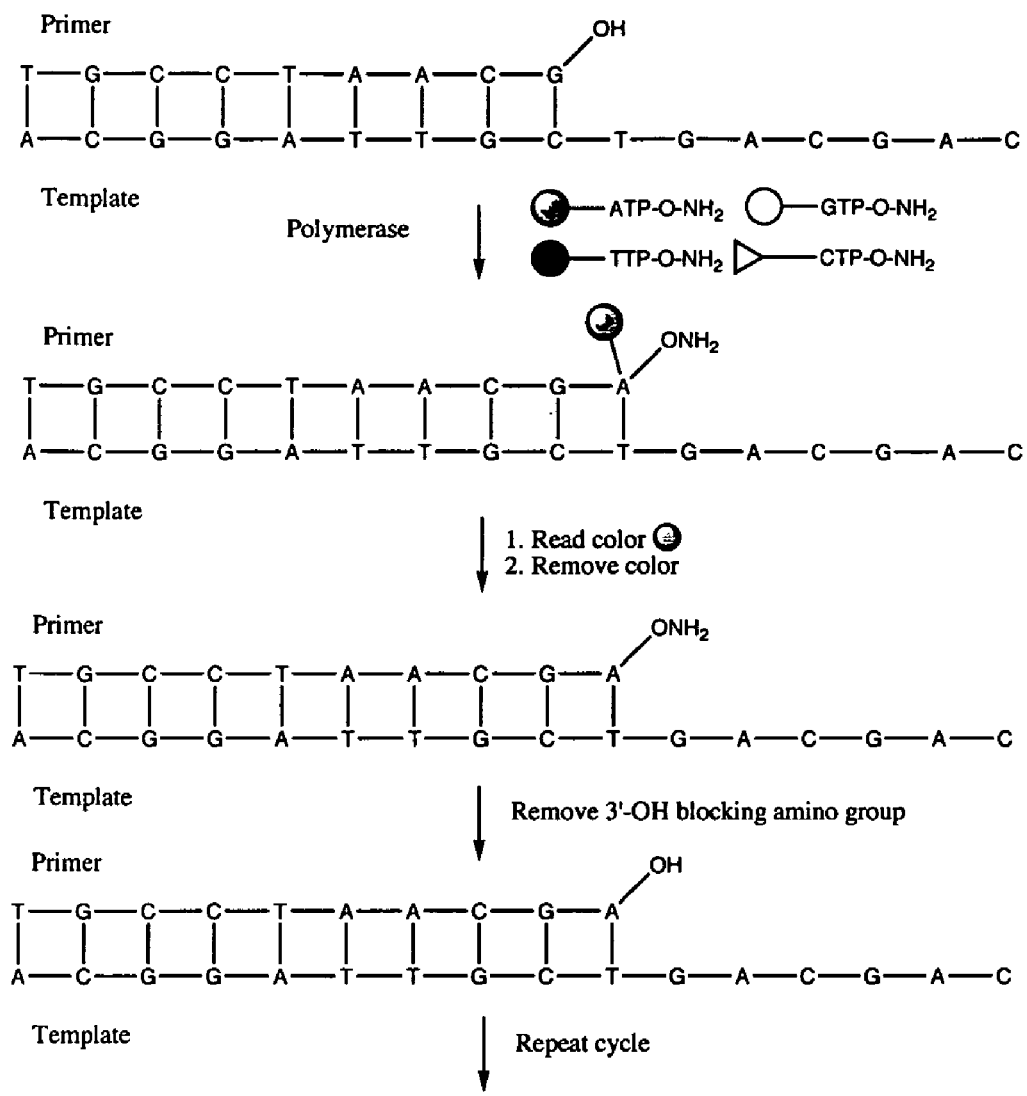
FIG. 1. Schematic for sequencing-by-synthesis using the 3'-$ONH_2$ group as a small, removable 3'-blocking group. The circles and triangles represent fluorescent groups having different colors. The 3'-blocked fluorescently tagged nucleotide is incorporated by a DNA polymerase. Chain termination then stops, because of the 3'-blocking group. The fluorescence color is read (determining which nucleotide was added), the fluorescent group is removed, and the 3'-OH is deblocked. The cycle can then be repeated.

To implement this invention, the 3-O-amino group is used as a removable protecting group for the sequencing-by-synthesis scheme (FIG. 1). The 3'-O-amino group is chosen because it is as small a moiety as can be imagined to form a stable 3'-O blocking group. The small size of the 3'-modification makes it most likely to be accepted by DNA polymerases during template-directed DNA polymerization [Hen04].

Further, contact by DNA polymerases with the 3'-end of the incoming triphosphate is frequently made with an amino acid with an aromatic side chain (Phe or Tyr) [Gar99]. The size of this can be reduced (to His), generating the possibility that if any particular natural polymerase does not work, then these can be mutated, followed by a round of in vitro directed evolution [Gha01], to generate polymerases that accept 3'-O-amino triphosphates with acceptable specifications.

A working sequencing-by-synthesis system that permits parallel (for example, a 100×100 array) sequencing or single nucleotide sequencing would be extremely useful, provided that the reads are >25 nucleotides in length). Even if the reads are short, sequencing-by-synthesis could be very useful in the laboratory and, perhaps, in personalized medicine. For example, one can imagine the use of a sequencing-by-synthesis chip for resequencing a specific locus within a genome to identify polymorphisms in a population.

Figure 2:
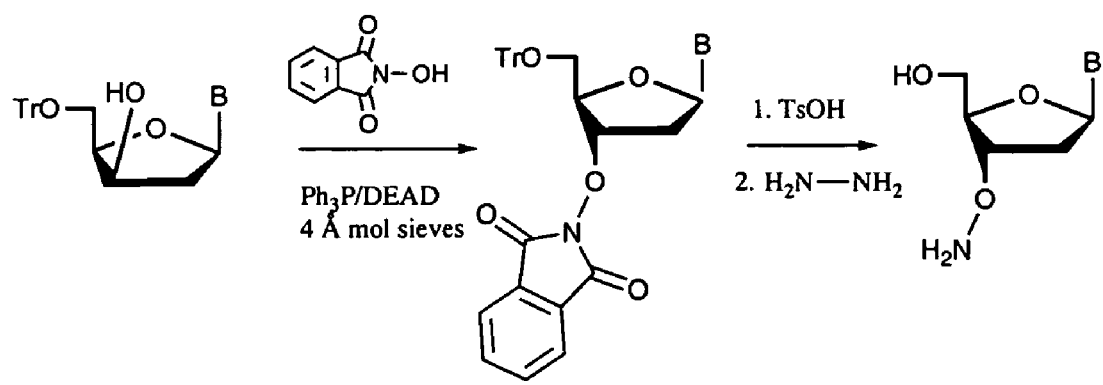
FIG. 2. Schematic describing the synthesis of 3'-O-amino-2'-deoxynucleosides. See [Kon85][Coo94][Bur94][DeC90].

The hydroxylamine functionality is stable in water, and displays several other advantages:

(a) A set of 3'-O-amino-2'-deoxynucleosides (FIG. 2) is already known in the literature [DeC90][Kon85][Bur94][Coo94]. They are directly synthesizable from the xylo-2'-deoxyribonucleosides via a Mitsunobu reaction with N-hydroxyphthalimide (FIG. 2). From this work, we know that the O—NH$_2$ group is compatible with DNA bases (pace the ability of hydroxylamine and methoxyamine to be mutagenic; see below).

(b) The 3'-O-amino-2'-deoxynucleoside blocking group is small, even smaller than the speculative —OSH unit (which was considered) and the azido unit (which is incorporated by reverse transcriptases when they accept azidothymidine triphosphate, for example).

(c) The 3'-O-amino-2'-deoxynucleoside functionality has much of the hydrogen bonding potential of the 3'-OH group. While not wishing to be bound by theory, these derivatives may form a network of hydrogen bonds to the catalytic magnesium ion, as suggested by crystallography for the natural substrate, and therefore fitting into the active site of various polymerases.

(d) In some cases, a polymerase can be improved by replacing the Phe or Tyr (depending on the polymerase) [Eva00][Gar04] that blocks the 3'-position of the incoming triphosphate with a slightly smaller aromatic group, H is or Phe (respectively).

(e) A large number of reagents are known that cleave the N—O linkage in hydroxylamines and O-alkoxyamines. These are discussed in greater detail below. Oxidative conditions are provided by bleach, nitroso compounds, iodate, or potassium ferrate in 1 M NaCl, 50 mM potassium phosphate buffer, 25° C.; this generates the free —OH group and N$_2$O, which is trapped. Reducing agents include catalytic hydrogenation. The preferred approaches include addition-elimination cycles where the amino group of the alkoxyamine adds to an electrophile (such as maleimide or a naphthoquinone) and then ejects the alcohol as a leaving group.

(f) The 3'-O-amino-2'-deoxynucleosides offer a handle that can permit the selection of polymerases that incorporate them, should mutagenesis studies not succeed. The water-oil emulsion system [Gha01] to select for thermostable polymerases is used to select polymerases that incorporate 3'-O-amino-2'-deoxynucleosides to their own gene where the genes are recovered by an aldehyde column that captures 3'-O-amino-2'-deoxynucleosides as oximes.

With this 3'-O blocking group, other features of the architecture of the state-of-the-art sequencing-by-synthesis approach could be adopted. In particular, the same cleavable linkers that hold the fluorescent labels to the nucleobases would be used. These linkers might also be designed such that they can be cleaved by whatever reagent was used to remove the amino group from the terminal 3'-O-amino-2'-deoxynucleoside.

Chemical Considerations

Using the O-amino 3'-blocking group in a sequencing-by-synthesis strategy is not constrained by the reactivity of N-alkoxyamines. These are nucleophiles, and simple members of this class of compound (hydroxylamine and methoxyamine in particular) are known to react with DNA, predominantly by replacing the exocyclic amino groups of cytosine and, to a lesser extent adenine, with the alkoxyamine to generate 4-methoxycytosine and 4-methoxyadenine [Koc69].

This is not a serious problem here. First, the reaction of alkoxyamines with cytidine proceeds slowly at neutral pH, even when the concentration of alkoxyamines is high. The reaction is slower with methoxyamine than hydroxylamine, and it is still slower with the secondary N-alkoxyamines, such as a 3'-ONH$_2$ unit on a nucleoside derivative. While not wishing to be bound by theory, it appears that these structural features explain why the 3'-O-amino unit does not react rapidly with cytosine and adenosine nucleosides [DeC90].

Basicity

For a typical alkoxyamine, pK$_a$≈4.6. The 3'-O-amino group is neutral at physiological pH.

Triphosphate Generation

Figure 3:
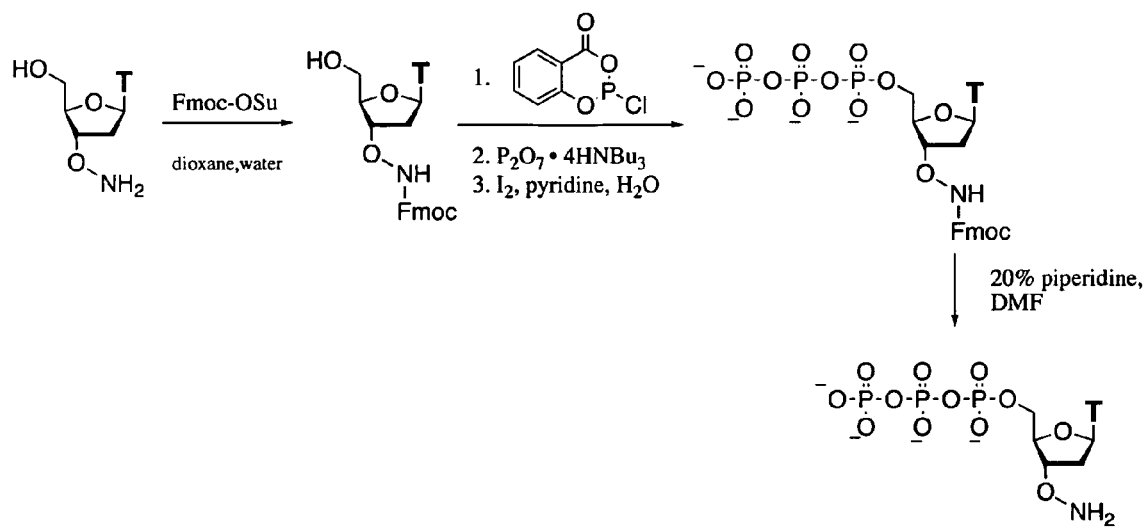
FIG. 3. The Ludwig-Eckstein synthesis of triphosphates.

The triphosphates of the 3'-O-amino-2'-deoxyribonucleosides are prepared using the Ludwig-Eckstein synthetic procedure [Lud89] (FIG. 3). Our preferred route for generating triphosphates applies the Ludwig-Eckstein procedure to the precursor where the O—NH$_2$ group is protected as an Fmoc amide, a trifluoroacetyl amide, or transiently as an oxime with acetone. Less preferably, but as an alternative, is to use the Ludwig-Eckstein procedure with the unprotected 3'-O-amino-2'-deoxynucleoside.

Cleavage of the N—O Bond to Regenerate the 3'-OH Group

A variety of reagents and conditions cleave N—O bonds. The instant invention offers a number of these, so that chemists can chose a procedure to fit the particular side chain chemistry that is used to append a readable tag to the nucleobases.

Most preferably, the reaction that removes the 3'-OH amino group is done in water. This is desired so that the integrity of the double helix is retained. It is possible, in a sequencing-by-synthesis architecture, to re-anneal following a treatment by a reagent that denatures the double helix, making the requirement for aqueous chemistry not absolute. This is less preferable, however, for practical use. Therefore, most preferable is an aqueous deblocking chemistry, with organic co-solvents present to less than 50% of the total by volume, under conditions where the double helix does not disassociate or precipitate. For example (depending on the salt concentration), solvents such as methanol or ethanol (to ca. 50%), tetrahydrofuran or dioxane (to 40%), or denaturants (e.g., dimethylformamide, dimethylsulfoxide to ca. 25%) may be used.

A substantial literature covers a large number of procedures to cleave the N—O bond of an R—$ONH_2$ unit. As summarized below, the instant invention offers ca. two dozen different reagents that might be used to cleave the N—O bond under conditions sufficiently mild that they will not degrade DNA, and not denature the primer-template duplex.

Most of these rely on the unique reactivity of the pair of heteroatoms (O—N), both having unshared pairs of electrons, reactivity that is not found elsewhere in DNA. Thus, the O—N unit has particularly low basicity, particularly good electron donation properties, and particularly high nucleophilicity. It shares these features with hydrazine and peroxide, as is well known in the art under the rubric of the "alpha effect". This means that against a variety of reagents, both electrophilic and oxidizing, the alkoxyamine group reacts first, before other parts of the DNA molecule. This suggests that competing reactivity is easily managed, using conditions that are beneficial in general for other reasons, including low reagent concentrations, low temperatures, rapid treatments, and rapid quenches. These conditions are desired by most sequencing-by-synthesis architectures.

Specifics of the N—O Substrate

Figure 4:
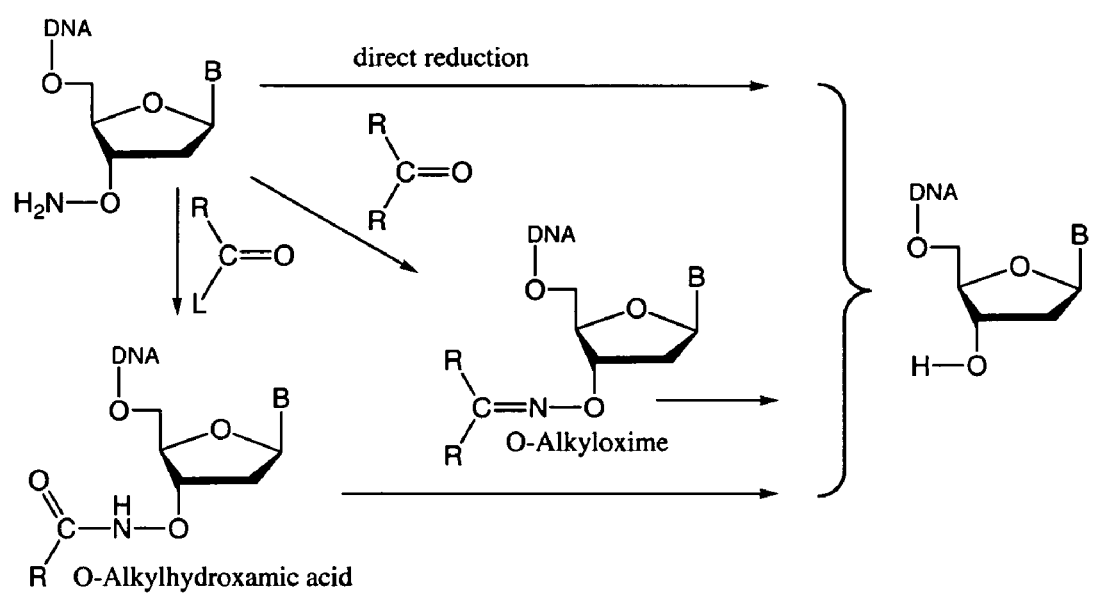
FIG. 4. Schematic for reactions to cleave the N—O bond.

The species that is being deblocked is known as an O-alkylhydroxylamine. Reagents are known for the cleavage of the N—O bond many other derivatives, including O-acyl hydroxylamines, N-acyl hydroxylamines, and oximes (where the O is —OH) (FIG. 4). These substrates have been chosen because they are intermediates in natural product syntheses of various types. Many of these are homogeneous, and many are known to work in aqueous media. However, it may be necessary to transform the 3'-terminally blocked —O—$NH_2$ unit into one of these derivatives. For example, preparing an oxime from the 3'-O—$NH_2$ unit is direct; one simply stirs with an aqueous solution of the appropriate ketone or aldehyde. The nature of the ketone or aldehyde can be adjusted to adjust the reactivity of the species. Preparing the O-alkylhydroxamic acid requires acylation. Here, mild acylation reagents in aqueous media are expected to prefer the hydroxylamine, with its enhanced nucleophilicity over the exocyclic amino groups of the nucleobases. Thus, reagents that cleave all three are considered here.

i. Oxidative Cleavage of the N—O Bond

The $NH_2$ group is susceptible to oxidation that leads to fragmentation. The simplest reagent is dilute hypochlorite in a process that has been known for half a century [Ril54]. In addition, nitric oxide and other nitrosating agents may be used. These have been reviewed recently by Corsano et al. [Cor01]. In particular, the reaction of O-alkoxyamines with nitroso compounds (e.g., nitrosobenzene) generates the diazo compound (in this case Ph—N=N—OR), which can be fragmented to give the alcohol ROH [Mas88][Mas90][Pat77][Ver91].

DNA is not easily degraded by hypochlorite and other oxidizing agents (see literature in this area [Ber90] [Hay71] [Hoy73] [Pat72] [Whi97] [Whi99]). Hypochlorite is a product of biological systems (through the reaction of hydrogen peroxide and chloride catalyzed by myeloperoxidase in mammalian neutrophils), as well as being ubiquitous in the environment (in swimming pools, food sanitizers, and the paper industry). In a relatively thorough recent study, Whiteman et al.

[Whi97] exposed calf thymus DNA to hypochlorite at 37° C. for one hour at pH 7.4, and quantitated various oxidation products of DNA. They found pyrimidine oxidation products (thymine glycol (cis/trans), 5-hydroxycytosine, 5-hydroxyuracil, 5-chlorouracil, and 5-hydroxyhydantoin), but not purine oxidation products (8-hydroxyguanine, 2- and 8-hydroxyadenine, FAPy guanine, FAPy adenine). Conversion was strongly dependent on concentration. At 0.1 mM HOCl concentrations, total modified base concentrations are between 1 and 5 nanomoles per mg of DNA. Thus, this represents a conversion of ca. 0.1%, in one hour at 37° C. As the alkoxylamine reaction is complete in seconds at lower temperature, this reaction has utility.

Other oxidizing agents are reported to cleave the N—O bond in oximes. These include Caro's acid [Mov00] and iodate [Mah97]. Iodate and DNA are quite compatible, as is well known from the fact that iodate is a product in the periodate-mediated cleavage of RNA, a process that is widely used in nucleoside chemistry. In these cases, the reaction appears to be done under aqueous conditions. In general, however, the procedure is well documented for oximes having a free OH group (see review in [Cor0].

N-Bromosuccinimide and N-bromoacetamide were also found to be efficient and selective reagents for the mild oxidative cleavage of oximes. Perchlorate and periodate are also able to convert a variety of oximes into the corresponding carbonyl compounds. These reactions are reported at 0° C., leaving alkaloid nitrogens untouched. But many of these reagents (such as the Dess-Martin periodinane) require a free OH on the oxime.

Our presently preferred method for oxidative cleavage is treatment with nitrous acid at pH 4-5, which cleaves the $ONH_2$ group at a rate over 100 times faster than it deaminates guanine, or treatment with a nitrite ester (e.g., ethyl nitrite) at pH 7-8.

ii. Reductive Cleavage of the N—O Bond

The classical way in synthetic organic chemistry to cleave the N—O bond is to treat the linkage with dihydrogen in the presence of a Pt or Pd catalyst [Cor83] [Nai94]. This reaction proceeds quantitatively, can occur in aqueous solvents, and leaves DNA undamaged.

The primary disadvantage of this process is that catalytic hydrogenation requires a heterogeneous catalyst which may not be accessible to DNA immobilized on a chip. No work has evidently been done to identify soluble catalysts that achieve the same end.

A variety of reagents have been used to reductively cleave N—O bonds under mild conditions. These are reviewed in [Khl03]. One of the earliest of these, introduced by Keck [Kec79], involves sodium amalgam. The reaction is reported in ethanol as solvent. Best results are obtained when the reaction mixture was buffered with four equivalents of sodium hydrogen phosphate.

Several low oxidation states metal cations that dissolve in water cleave N—O bonds. These were discovered in the late 1960's and early 1970's in programs to synthesize antibiotics where oximes were precursors. Many of these work in water under conditions where duplex DNA is expected to be stable.

One of these was provided by Timms and Wildsmith in a process that cleaved the N—O bond of an oxime in a precursor for the synthesis of erythromycin [Tim71]. Here, heterogeneous catalysts were explicitly not desired (as is the case in sequencing-by-synthesis), and special effort was made to obtain a reagent that could exist in homogeneous solution with the reactant. Clean and quantitative conversion was obtained using a 15% solution of $TiCl_3$ in water buffered with sodium acetate. Two equivalents of the reagent were required, and the reaction was easily followed by the loss of the characteristic color of titanium (III). Conversion was complete within five minutes at room temperature. The only negative feature of this reaction is the fact that it is reported for a free oxime, rather than an O-alkyloxime.

Timms and Wildsmith also report two other low valent metals suitable for reduction of an oxime in aqueous solution. These are divalent vanadium (prepared by Zn/Hg reduction of vanadyl sulfate), samarium [Chi96] and divalent chromium (where acetate buffer was not used). Molybdenum hexacarbonyl $Mo(CO)_6$ is widely used in synthesis, as it cleaves the O—N bond where both the oxygen and the nitrogen have substitutents. This reagent is used in water-acetonitrile mixtures [Nit85] [Khu04] [Mar05] [You06]; the species is not soluble in pure water. Active agents having the formula $Mo(CO)_n(NCR)_{6-n}$, which are more soluble in water, may also be used.

The fact that $TiCl_3$ works directly on an oxime was cited by [Tim71] as an advantage over other procedures that use low valent metals as reducing agents, but are reported for O-acylated oximes. The procedure of Corey and Richman [Cor70], which involves the treatment of an O-acyl oxime with chromium (II) cleaves the N—O bond of O-acetyl oximes in aqueous solution. The reaction Is reported to proceed in high yield at room temperature over 24 hours. Only incomplete experimental details are provided in the original paper; in particular, the paper does not report whether the reaction also works with O-alkylated oximes. Another potentially suitable method was offered by Keck [Kec95a,b] using $SmI_2$.

Some of these reagents may have utility to regenerate the 3'-hydroxyl group, allowing the next cycle in the sequencing-by-synthesis strategy to occur. In these procedures, the first step involves the reaction of a carbonyl compounds with the $NH_2$ group to create an oxime. Acetone appears to be perfectly acceptable for this purpose. This creates 2'-aminopropane as a side product, which is innocuous. A larger aldehyde having fluorescence can also be used. This generates the corresponding amine, which can be detected as a way to monitor the progress of the reaction. In the second step, the trivalent cation is introduced as its chloride salt in dilute aqueous solution.

iii. Addition-Elimination Sequences

Figure 5:
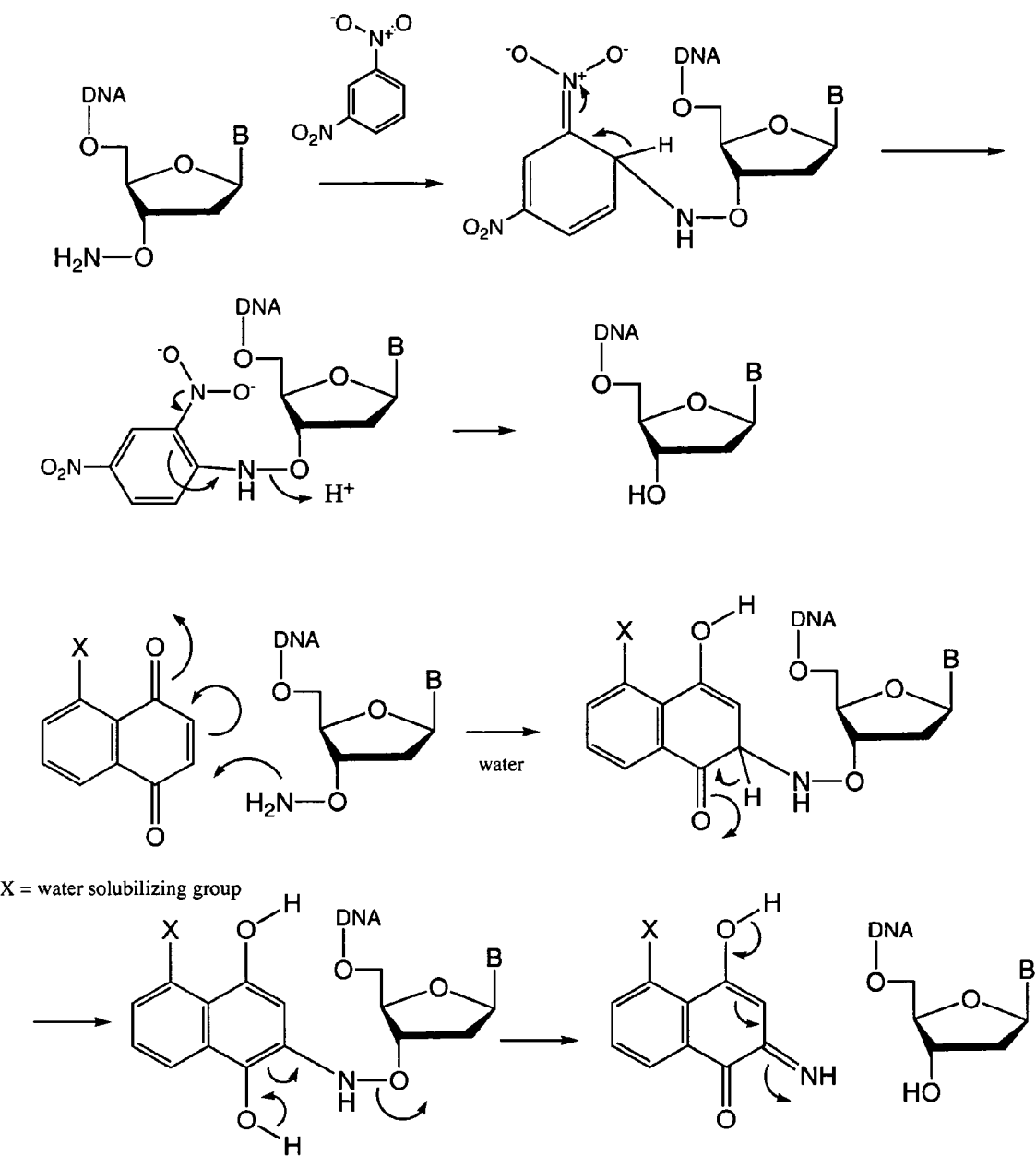
FIG. 5. Some typical addition-elimination strategy for cleaving the N—O bond at the 3'-end of the DNA molecule. The strategy takes advantage of the high nucleophilicity of the alkoxylamine nitrogen and a "pull-push" curved arrow electron flow [Nik00][Bit94].
Figure 7:
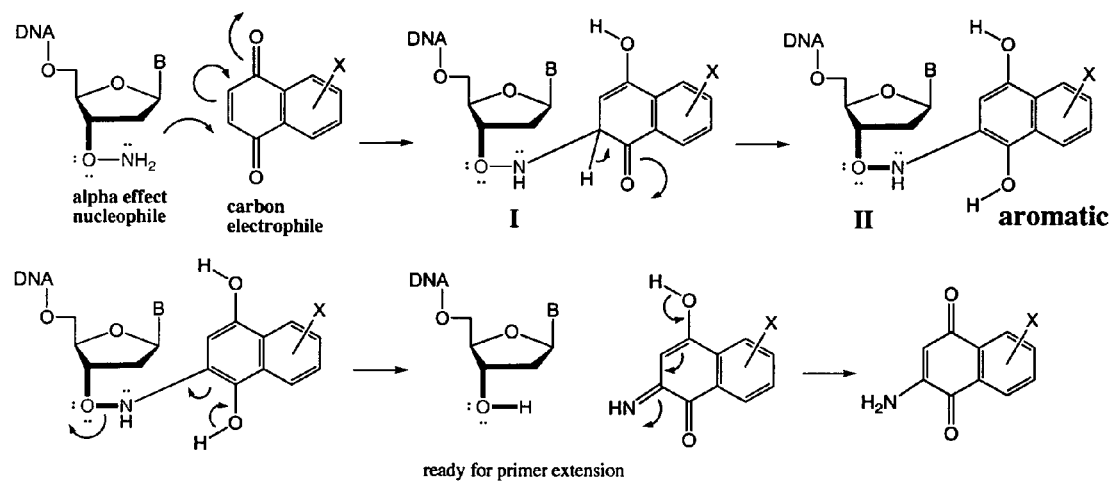
FIG. 7. Naphthoquinone carboxylates (X=$COO^-$) and sulfonates (X=$SO_3^-$) designed to remove the 3'-$ONH_2$ group from a DNA molecule with the 3'-OH group blocked by an amino group.

A third approach, which is presently preferred, involves neither oxidation nor reduction, but rather an addition/elimination sequence. This can be done with a wide range of electrophiles. The general strategy involves the attack of the amino group of the alkoxylamine upon an electrophilic molecule that, after the appropriate arrowisms, produces a push of electrons that ejects the oxygen of the alkoxylamine as a leaving group. A schematic for these is shown in FIG. 5. The electrophile can be maleimide [Sek97] [Sek99], nitrobenzene [Nik00], or nitroolefins [Ima96] [Ima97].

One method potentially involves the reaction of the O-alkoxylamine with a quinone, preferably a 1,4-naphthoquinone [Bit94], and more preferably a 1,4-naphthoquinone that carries on the second ring an ionic group (such as a sulfonate or carboxylate group) that makes the quinone soluble in aqueous media. The reactions leading to the removal of the amino group from the oxygen all proceed under mild conditions (FIG. 5). While not wishing to be bound by theory, the utility of this reagent may be diminished by the presence of multiple electrophilic sites in the species, which creates dead-end products that are not easily converted to the desired product.

iv. Novel Reaction Sequences

While the reagents described give the new compositions utility in a variety of settings, the instant application discloses additional reagents for cleaving a 3'-$ONH_2$ blocking group. These fall into two classes.

Figure 14:
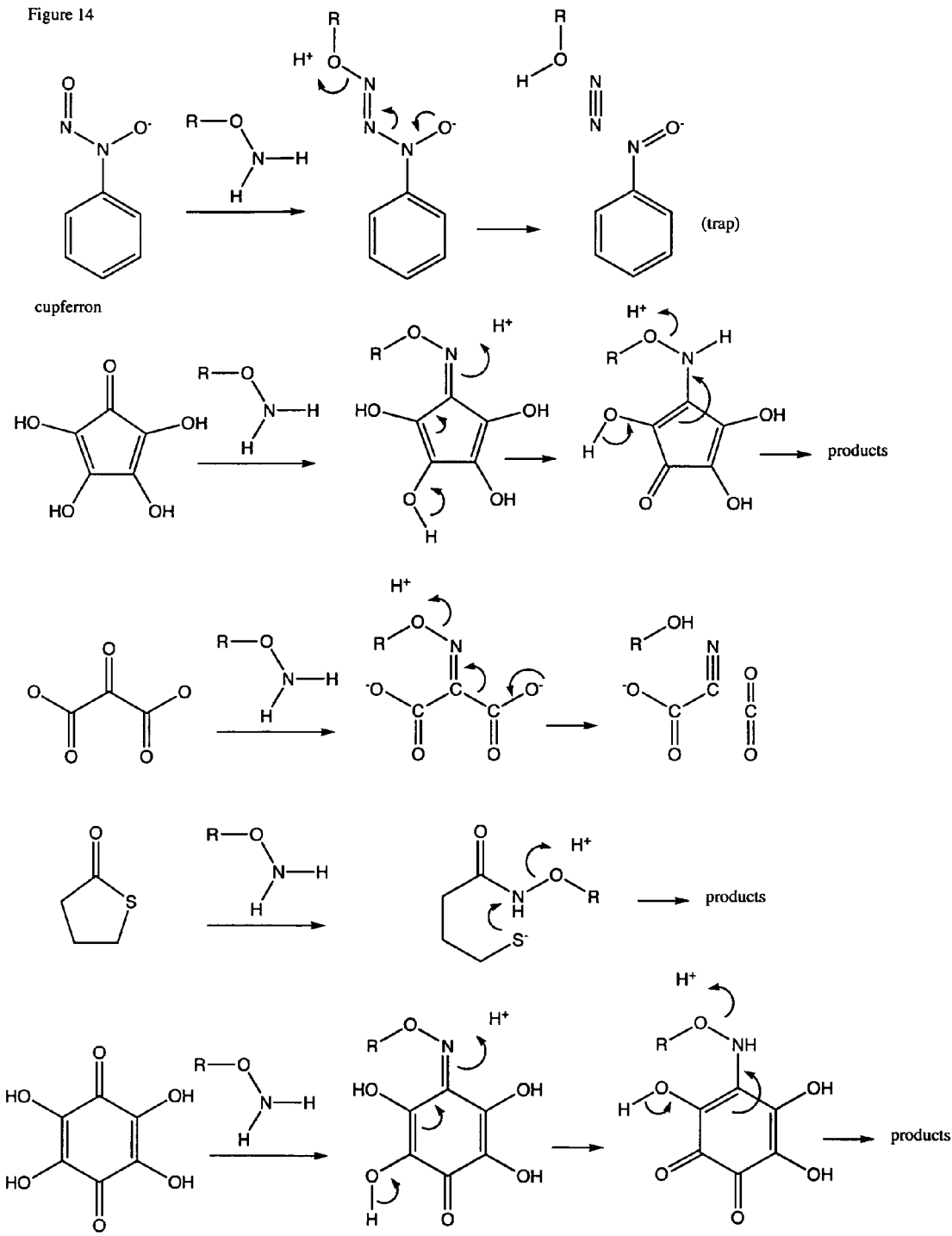
FIG. 14. Methods for removing the 3'-$ONH_2$ group from a DNA or RNA molecule with the 3'-OH group blocked by an amino group that do not involve a second reagent.

Class 1. Reagents that react directly with the 3'-$ONH_2$ blocking group, and generates the 3'-OH unit without the isolation of an intermediate, or the addition of a subsequent reagent in a second step. These include reagents shown in FIG. 14. While not wishing to be bound by theory, these figures also illustrate mechanisms by which these reagents are presumed to act.

Figure 15:
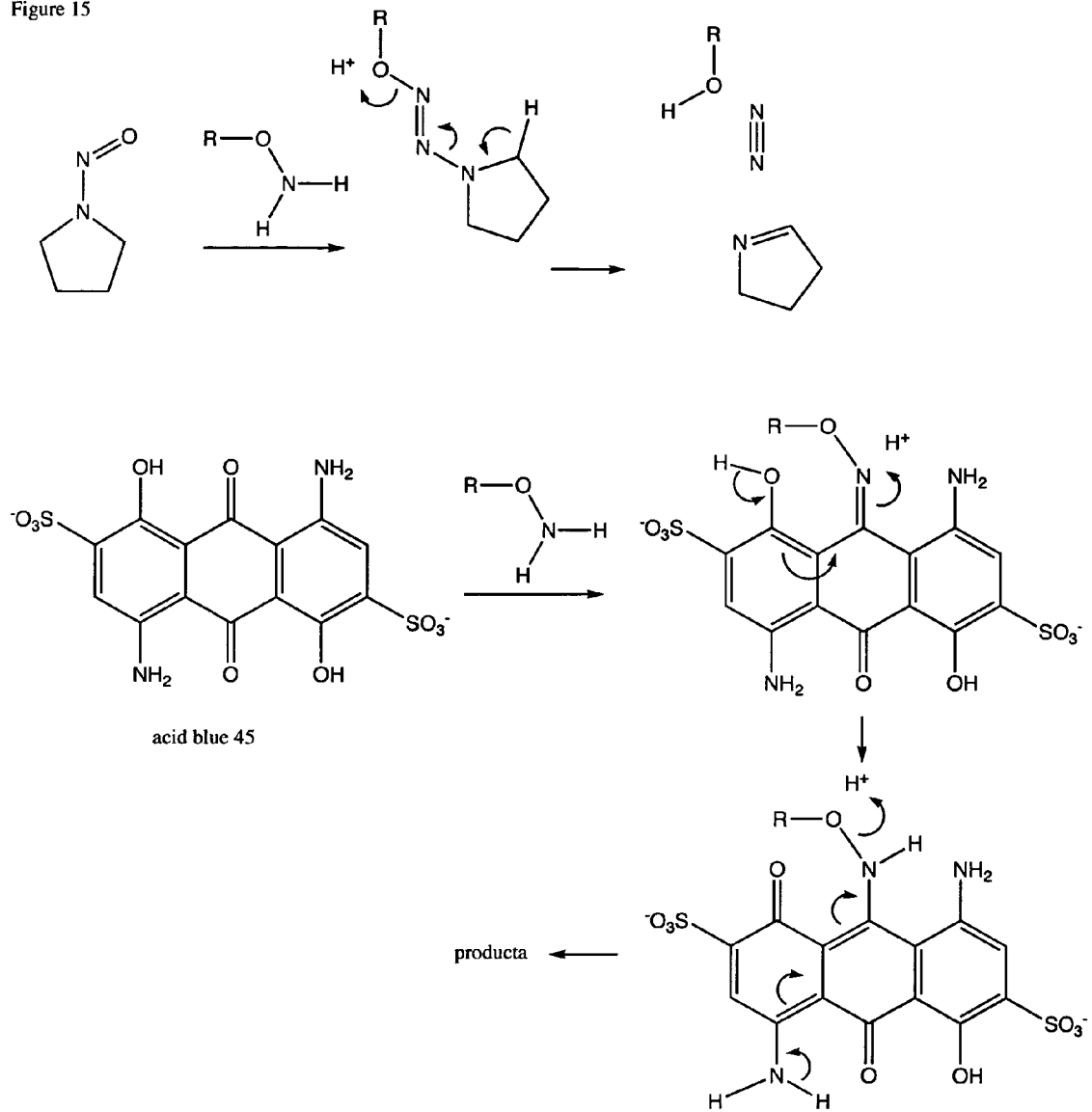
FIG. 15. Methods for removing the 3'-$ONH_2$ group from a DNA or RNA molecule with the 3'-OH group blocked by an amino group that do not involve a second reagent.
Figure 16:
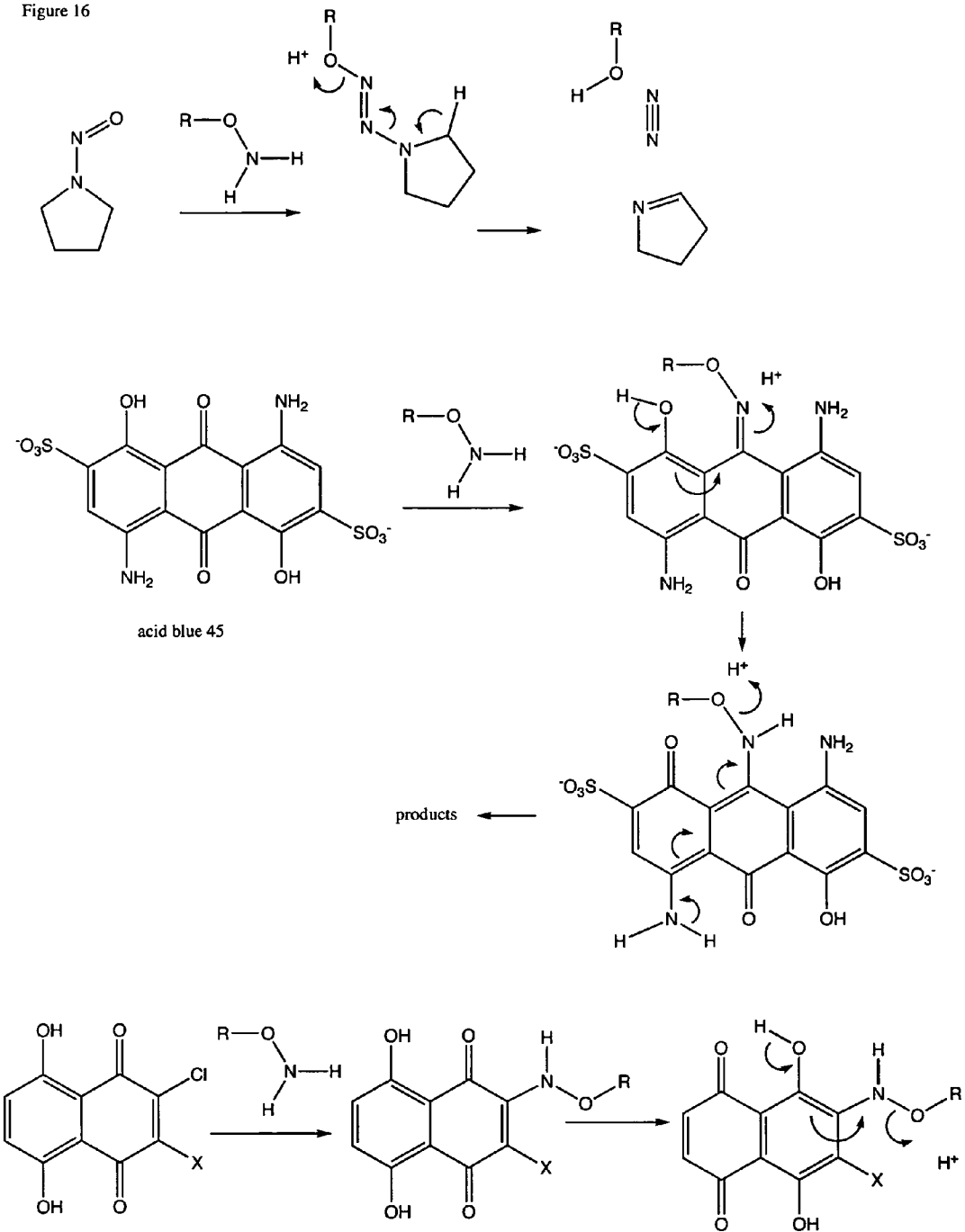
FIG. 16. Methods for removing the 3'-$ONH_2$ group from a DNA or RNA molecule with the 3'-OH group blocked by an amino group that do not involve a second reagent.
Figure 17:
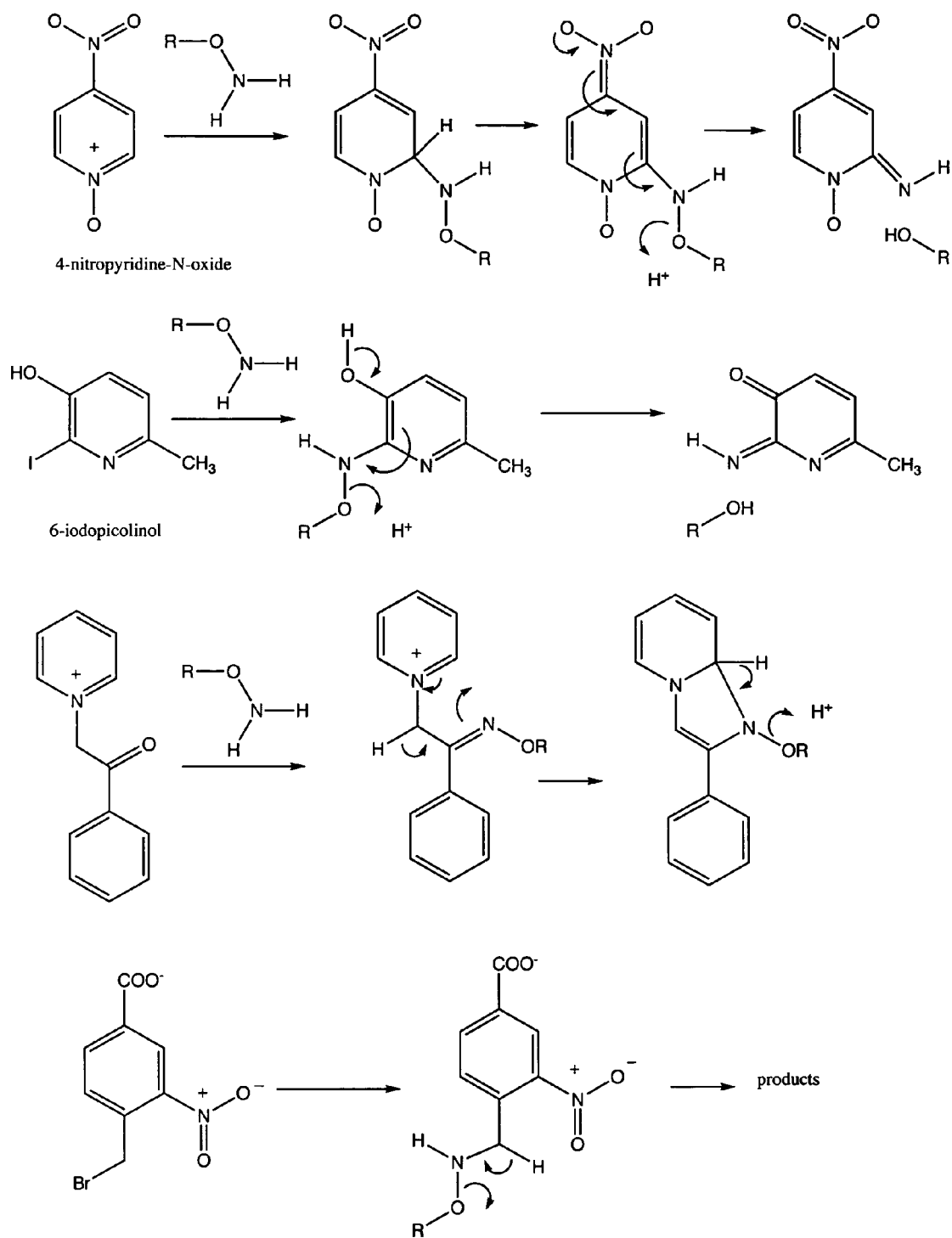
FIG. 17. Methods for removing the 3'-ONH$_2$ group from a DNA or RNA molecule with the 3'-OH group blocked by an amino group that do not involve a second reagent.
Figure 18:
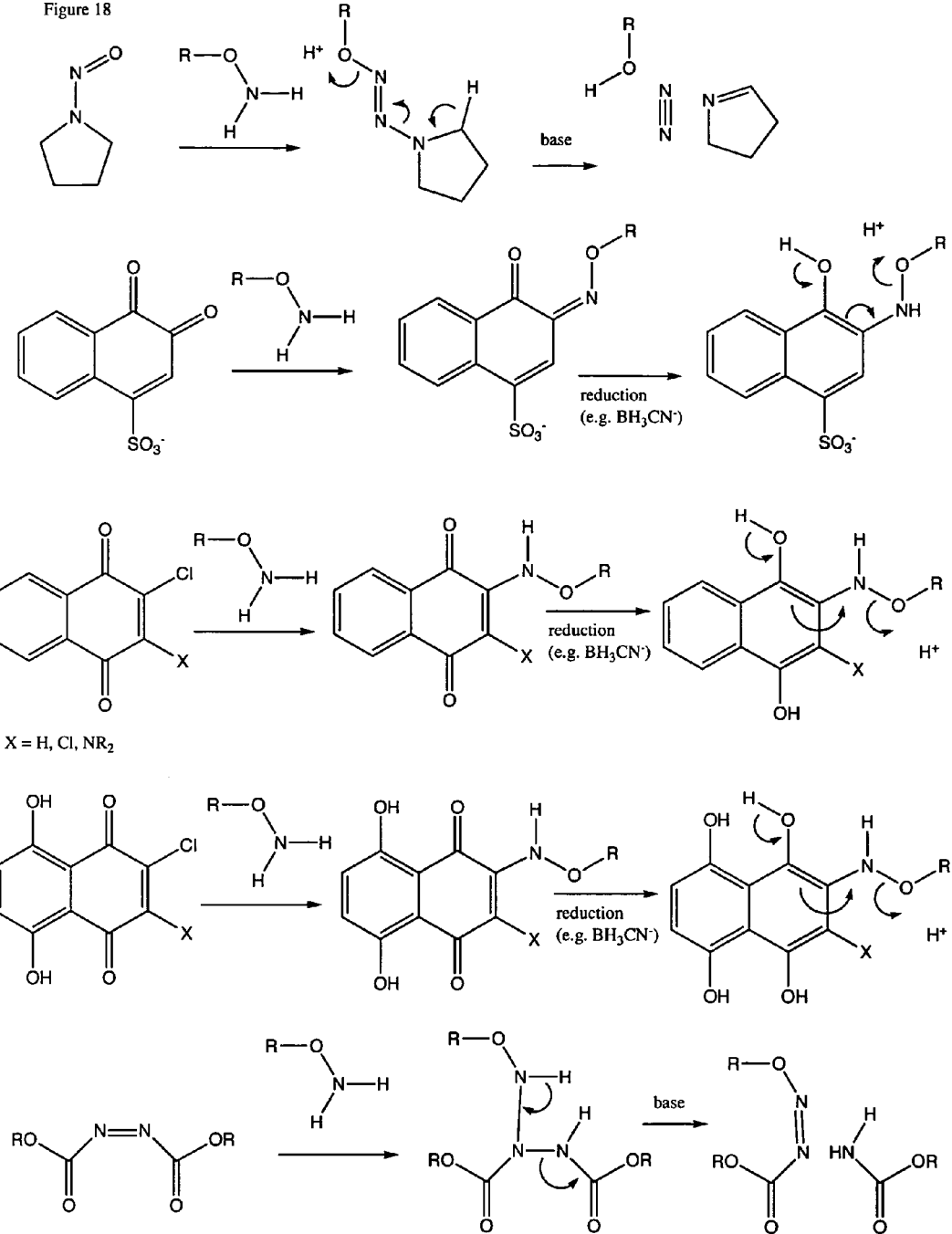
FIG. 18. Methods for removing the 3'-ONH$_2$ group from a DNA or RNA molecule with the 3'-OH group blocked by an amino group that do involve a second reagent.

Class 2. Reagents that react directly with the 3'-$ONH_2$ blocking group to form an intermediate, which then generates the 3'-OH unit. These include reagents shown in FIG. 15. While not wishing to be bound by theory, these figures also illustrate mechanisms by which these reagents are presumed to act.

Fluorescent Tags

We next consider fluorescent tags that might be used in conjunction with a 3'-$ONH_2$ reversible blocking group. Classically, fluorescent groups are appended to the five position of pyrimidines, or to the 7-position of 7-deaza purines. Many groups have developed chemistry for preparing these classical derivatives (see for example [Hob91], see also our work [Hel02] [Roy04] and references cited therein for a "two moving target" optimization of polymerases and the 5-position linker). Tags at this position are accepted by polymerases [Hel02], and fluors at this positions are combined with modifications in the sugar to do dideoxy sequencing.

In practice, any linker that can be cleaved to release the fluorescent product allows the loss of the fluor prior to the next extension reaction, preventing the fluor from cycle n from confusing the signal from the fluor appended at cycle n+1. Alternatively, with strategic choice of the fluor, the fluor can itself be destroyed by chemical transformation, including by reduction (e.g. of cyanine fluors) or by bleach.

A second consideration reflects the fact that the rule-based molecular recognition properties displayed by DNA and RNA are unique in chemistry, and easily disrupted. As was demonstrated in earlier work [Hel02], addition of extensive functionality to every nucleobase may disrupt the rule based molecular recognition. Therefore, the preferred strategy removes as much of the tag as possible at each cycle, and arranges to have what is left behind be as hydrophilic as possible. This is, of course, in addition to the need to have inexpensive and readily accessible linkers.

The presently preferred linker, after cleavage, leaves behind a —CH═CH—CH₂OH group. This is preferable to the —CH═CH—CH₂—NH₂ group, which places a positive charge on the side chain. It is also preferable to the —CC—CH₂—OH, —C—CH₂—SH, and —CC—CH₂—NH₂ units, for reasons of record [Hel02], although these may also be used. Last, the longer linkers —CC—CH₂—CH₂—OH, —CC—CH₂—CH₂—SH, —CC—CH₂—CH₂—NH₂, —CH═CH—CH₂—CH₂—NH₂, H═CH—CH₂CH₂—OH, and —CH═CH—CH₂—CH₂—SH linkers, which have enhanced stability, although they each leave an extra atom once cleavage is complete.

Each of these linkers can carry a fluorescent tag appended by an ester, amide, or disulfide linkage, appropriately. The presently preferred —CH═CH—CH₂OH linking group has certain advantages, however. First, the allyl group stabilized duplexes when attached to the 5-position of pyrimidines. Further, the —OH terminus is uncharged, yet hydrophilic.

Most significantly, however, the —OH terminus can be left behind with the reagent that cleaves the 3'-ONH₂ group, if the fluor is attached to the linker via the —O—NH-Tag unit. This can be coupled to the 5-iodopyrimidine and the 7-iodo-7-deazapurine units using the synthetic intermediate where the Boc-NH—CH₂—CH₂—N-Fmoc unit, which is then attached to a standard fluor (a cyanine dye for single molecule sequencing, or a rhodamine, bimane, dyes with large Stokes shift, and other molecules). These are the presently preferred linkers in large part because they can be cleaved from the nucleobase using the reagent that is used to cleave the 3'-O blocking group.

EXAMPLE

Synthesis of the 3'-O-amino-2'-deoxynucleosides

Kondo et al. nearly two decades ago reported the synthesis of the first 3'-O-amino-2'-deoxynucleoside [Kon85]. Subsequently, De Clerq prepared a complete set of 3'-O-amino-2'-deoxynucleosides, and reported their syntheses in the European patent literature [DeC90]. The team at Isis led by Cook also generated these as well as part of their program in antisense nucleic acid analogs [Coo94]. Finally, in 1994, Burgess and his coworkers reported the synthesis of dinucleotides joined via an N—O linker in a synthesis that began with the 3'-O-amino-2'-deoxynucleoside [Bur94] (FIG. 2, see also [Oga98]).

These research groups prepared these compounds because they were seeking to generate nucleic acid analogs where the anionic phosphodiester bond was replaced by an uncharged linker. It does not appear that they considered the possibility of using the 3'-O-amino moiety as a blocking group for a sequencing-by-synthesis architecture. The uncharged N-o linker was viewed as a useful replacement for the charged phosphodiester linker. Coupling could be easily achieved via reaction of the 3'-O-amino-2'-deoxynucleoside with an aldehyde on the next nucleotide building block.

These and other uncharged DNA analogs were hoped to be able to passively enter cells, and to continue to bind to natural DNA and RNA following Watson-Crick pairing rules. The antisense strategy fell out of favor when this was found not to be the case. Nevertheless, the activity left behind a rich literature, which makes the synthesis of the needed 3'-O-amino-2'-deoxynucleosides well precedented.

This notwithstanding, no route was available for preparing the triphosphates, which are new compounds disclosed in the instant invention for the first time. These can be prepared by the route disclosed in FIG. 3).

The xylo-nucleoside analogs are synthesized under mild conditions from the 5'-trityl- or 5'-dimethoxytrityl-nucleoside derivatives by Mitsunobu reaction with benzoic acid, followed by aminolysis of the resulting benzoate with NH₄OH. Representative procedures are given below:

5'-O-Trityl-xylothymidine. Thymidine (4.8 g; 20 mmol), DMAP (1.2 g; 10 mmol) and triethylamine (5.6 mL; 40 mmol) are dissolved in anhydrous pyridine (70 mL) at room temperature. Tritylchloride (11.2 g; 40 mmol) is added and the mixture is stirred at room temperature, leading to the precipitation of HCl salts. After 3 days, TLC(CH₂Cl₂: MeOH=10:1) is used to show ca. 90% conversion. The mixture is then cooled to 0° C. Methanesulfonyl chloride (1.9 mL; 25 mmol) and triethylamine (3.5 mL; 25 mmol) are added and the mixture is stirred at room temperature for 2 h. The HCl salts are removed by filtration, and the filtrate is concentrated in vacuo. Ethanol (130 mL) and aqueous NaOH (1.5 M; 65 mL) are added and the mixture is heated at reflux for 2 h. The reaction is quenched by the addition of aqueous HCl (1 M; 80 mL) and the solvents are removed in vacuo. Aqueous work-up (CH₂Cl₂) and flash liquid chromatography (silica, eluent CH₂Cl₂:MeOH=30:1 to 10:1) gives 5'-O-trityl-xylothymidine (expected 5.9 g; 61% overall) as a colorless foam. ¹H-NMR (CDCl₃; 300 MHz): δ(ppm)=1.74 (d, J=0.8 Hz, 3H); 2.22 (dd, J=1.9, 15.0 Hz, 1H); 2.46-2.59 (m, 1H); 3.28 (br s, 1H); 3.45-3.68 (m, 2H); 4.02-4.08 (m, 1H); 4.40-4.44 (m, 1H); 6.17 (dd, J=2.2, 8.0 Hz, 1H); 7.20-7.50 (m, 15H); 7.60 (d, J=1.0 Hz, 1H); 9.59 (br s, 1H).

5'-O-Trityl-3'-O-phthalimido-thymidine. 5'-O-Trityl-xylothymidine (1.9 g; 4 mmol), triphenylphosphine (1.3 g; 5 mmol) and N-hydroxyphthalimide (815 mg; 5 mmol) are dissolved in THF (60 mL) at 0° C. Diisopropylazodicarboxamide (DIAD, 965/L; 5 mmol) is added drop wise, and the reaction mixture is stirred as the temperature rises from 0° C. to room temperature. After 15 h, the reaction was quenched by the addition of H₂O (100 μL), and the reaction mixture is concentrated in vacuo. Flash liquid chromatography (silica, eluent EtOAc:hexanes=1:1 to 3:1) gives 5'-O-trityl-3'-O-phthalimido-thymidine (expected 3.4 g; ca 3.5 mmol nucleoside; 88%) as a colorless foam. The material may be contaminated with Ph₃P═O, but is used for the next step without further purification. ¹H-NMR (CDCl₃; 300 MHz): a (ppm)=1.48 (d, J=0.9 Hz, 3H); 2.34-2.42 (m, 1H); 2.84 (ddd, J=1.7, 4.8, 14.0 Hz, 1H); 3.48 (ddd, J=3.2, 10.0, 35.0 Hz, 2H); 4.50-4.54 (m, 1H); 5.07-5.13 (m, 1H); 6.60 (dd, J=5.6, 8.0 Hz, 1H); 7.16-7.85 (m, 38H); 9.08 (br s, 1H).

3'-O-Amino-thymidine. Hydrazine monohydrate (7 mL) is added to a suspension of 5'-O-trityl-3'-O-phthalimido-thymidine (2.9 g; ca. 3 mmol nucleoside, contaminated with some Ph₃P═O) in ethanol (30 mL), and the solution is heated under reflux for 2 h. The ethanol is removed in vacuo and the resulting mixture is partitioned between CH₂Cl₂ (100 mL) and aqueous NaCl (50% sat.; 100 mL). The organic phase is separated and concentrated in vacuo to give a colorless foam, which is redissolved in anhydrous dichloromethane (20 mL). A solution of zinc chloride etherate (1 M in Et₂O; 30 mL; 30 mmol) is then added. After a few minutes, the product starts to precipitate. After 30 minutes, the solution is diluted with CH₂Cl₂ (100 mL) and the precipitate removed by filtration. The solids are partitioned between water (20 mL) and CH₂Cl₂ (20 mL). The aqueous phase is separated and lyophilized. The crude product is purified by reverse phase HPLC(C₁₈, gradient 0-5% acetonitrile in water over 20 minutes) to give 3'-O-amino-thymidine (expected 340 mg; 44% overall) as a colorless foam. ¹H-NMR (DMSO-d₆; 300 MHz): δ(ppm)=1.77 (d, J=0.7 Hz, 3H); 1.97-2.07 (m, 1H); 2.29 (ddd, J=0.7, 5.9, 13.7 Hz, 1H); 3.50-3.66 (m, 2H); 3.99-4.03 (m, 1H); 4.16-4.20 (m, 1H); 5.08 (t, J=5.1 Hz, 1H); 6.10-6.16 (m, 3H); 7.73 (d, J=1.0 Hz, 1H); 11.27 (br s, 1H). $^{13}$C-NMR (DMSO-d$_6$; 75 MHz): a (ppm)=12.3, 35.7, 62.1, 83.7, 83.7, 83.9, 109.5, 136.0, 150.5, 163.7.

Triphosphate Generation

Triphosphates are synthesized using an adaptation of the Ludwig-Eckstein procedure. The amino group is first protected by Fmoc to prevent phosphorylation of this amine. The protection also enhances the solubility of the nucleoside.

3'-O-(Fmoc)amino-thymidine. 3'-O-Amino-thymidine (129 mg; 0.5 mmol) and sodium carbonate (53 mg; 0.5 mmol) are dissolved in water (1.5 mL). Fmoc-OSucc (202 mg; 0.6 mmol) is dissolved in dioxane (1.5 mL). The two solutions are then mixed, and the mixture is stirred at room temperature for 3 h. The mixture is partitioned between EtOAc (20 mL) and aqueous NaCl (50% sat., 20 mL). The organic phase is concentrated in vacuo and the residue purified by flash liquid chromatography (silica, eluent EtOAc:hexanes=1:1 to pure EtOAc) to give 3'-O-(Fmoc)amino-thymidine (expected 122 mg; 52%) as a colorless solid. $^1$H-NMR (CDCl$_3$; 300 MHz): δ(ppm)=1.92 (d, J=1.0 Hz, 3H); 2.45 (m, 1H); 2.62 (m, 1H); 3.75 (m, 1H); 3.92 (m, 1H); 4.16 (d, J=2.4 Hz, 1H); 4.24 (t, J=6.0 Hz, 1H); 4.57 (t, J=5.7 Hz, 2H); 6.06 (dd, J=6.4, 8.8 Hz, 1H); 7.29-7.48 (m, 4H); 7.58 (d, J=7.8 Hz, 2H); 7.77 (d, J=7.5 Hz, 2H); 8.13 (br s, 1H).

3'-O-(Fmoc)amino-thymidine-5'-triphosphate. Following the Ludwig-Eckstein procedure, 3'-O-(Fmoc)amino-thymidine (111 mg; 0.23 mmol) is rendered anhydrous by coevaporation with pyridine. The residue is redissolved in anhydrous pyridine (230 μL) and anhydrous dioxane (690 μL). A freshly prepared solution of 2-chloro-4H-1,2,3-dioxaphosphorin-4-one (73 mg; 0.36 mmol) in anhydrous dioxane (210 μL) is then added at room temperature under stirring. After 10 minutes, a mixture of bis(tributylammonium) pyrophosphate (127 mg; 0.27 mmol; 1.6 eq. Bu$_3$N per pyrophosphate) and tributylamine (212 μL; 0.89 mmol) in anhydrous DMF (640 μL) was added. After a further 10 minutes, a solution of diiodine in pyridine/water (98/2, v/v; 1% iodine; 4.5 mL) is added. After 15 minutes, excess diiodine is reduced by the addition of a few drops of aqueous Na$_2$SO$_3$ (5%; ca 0.3 mL). The mixture is then concentrated in vacuo. The residue is redissolved in water (2 mL) and purified by rp-HPLC(C$_{18}$, gradient 0-35% acetonitrile in 10 mM triethylammonium acetate over 37 minutes) to give 3'-O-(Fmoc)amino-thymidine-5'-triphosphate as a colorless foam. $^1$H-NMR (D$_2$O; 300 MHz): a (ppm)=1.72 (s, 3H); 1.81-1.91 (m, 3H); 3.91 (m, 3H); 4.01 (m, 1H); 4.29 (m, 1H); 4.41 (m, 1H); 5.89 (m, 1H); 7.11-7.20 (m, 4H); 7.39-7.57 (m, 5H). $^{31}$P-NMR (D$_2$O; 162 MHz): δ(ppm; H$_3$PO$_4$=0)=-12.4 (br s, 1P); -13.3 (br s, 1P); -24.9 (br s, 1P).

3'-O-Amino-thymidine-5'-triphosphate. 3'-O-(Fmoc) amino-thymidine-5'-triphosphate is dissolved in 20% piperidine in DMF (0.5 mL). The mixture is stirred at room temperature for 30 minutes and then concentrated in vacuo. The residue is redissolved in triethylammonium acetate buffer (aqueous, 10 mM; pH 7; 2 mL) and purified by rp-HPLC (C$_{18}$, gradient 0-21% acetonitrile in 10 mM triethylammonium acetate over 27 minutes) to give 3'-O-amino-thymidine-5'-triphosphate as a colorless foam. The purity of the product is confirmed by analytical ion-exchange chromatography (DEAE, gradient 0-1 M triethylammonium bicarbonate in water over 30 minutes). $^1$H-NMR (D$_2$O; 300 MHz): δ (ppm)=1.80 (s, 3H); 2.18 (m, 1H); 2.34-2.39 (m, 1H); 4.03-4.09 (m, 2H); 4.25 (m, 1H); 4.45 (m, 1H); 6.17 (dd, J=6.0, 9.1 Hz, 1H); 7.66 (s, 1H). $^{31}$P-NMR (D$_2$O; 162 MHz): δ (ppm; H$_3$PO$_4$=0)=-14.1 (br s, 1P); -16.3 (br s, 1P); -27.7 (br s, 1P). MS-ESI$^-$: [M-H]$^-$ calcd. for C$_{10}$H$_{17}$O$_{14}$N$_3$P$_3$, 496.0; found, 496.4.

Fluorescent Tags

Classically, fluorescent groups are appended to the 5-position of pyrimidines, or the 7-position of 7-deaza purines. A variety of chemistry is available for preparing these classical derivatives (see for example [Hob91]). Work in the Benner group (see [Hel02] [Roy04] and references cited therein) describe the "two-part" (or perhaps better named, the "two moving target" optimization of polymerases and the 5-position linker. Tags at this position are accepted by polymerases [Hel02], and fluors at this positions are combined with modifications in the sugar to do dideoxy sequencing.

Figure 8:
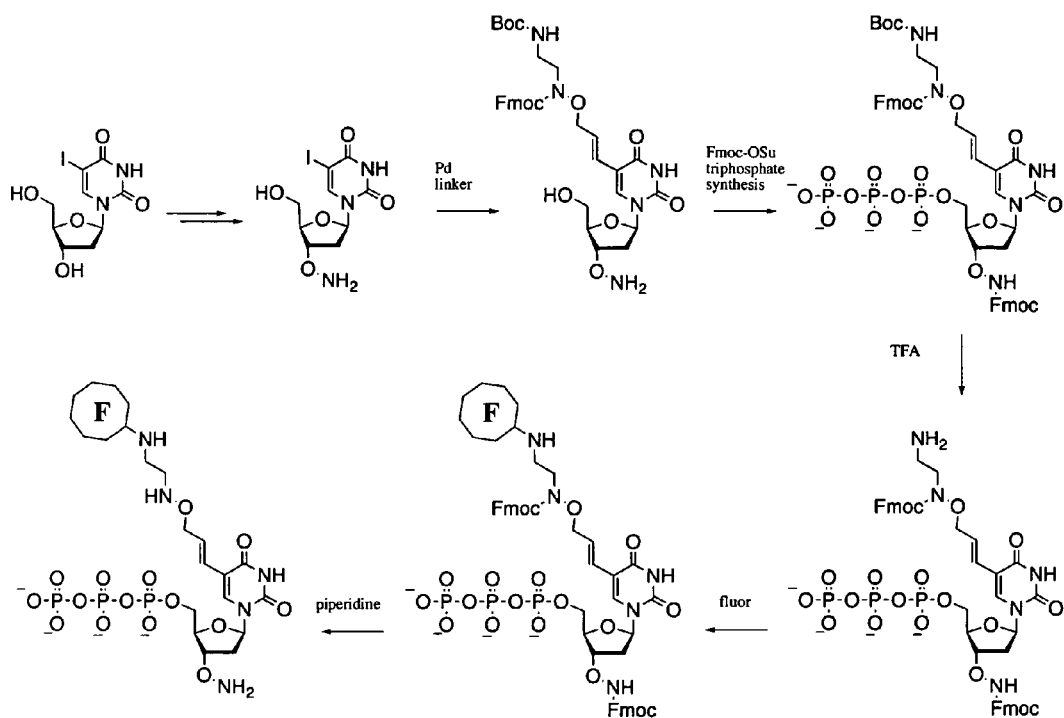
FIG. 8. Overall strategy for the synthesis of the 2'-deoxynucleoside-5'-triphosphates with 3'-O—$NH_2$ and a fluorophore attached to the nucleobase, here shown for the thymidine analog.

Disclosed here is one of several orthogonal protection strategies that allow for the attachment of the fluorescent tag onto the triphosphate without interference of the nucleophilic alkoxylamines (FIG. 8). Other strategies are easily envisioned by those skilled in the art. The nucleosides bearing an iodo substituent at the 5-position (pyrimidines) or 7-position (7-deazapurines) are either commercially available or well documented in literature [Hob91]. First, the 3'-O-amino group is introduced by the procedure outlined above. Next, the linker for the fluorophore or other tag is attached via a Heck coupling reaction [Dey01]. The linker contains an olefin to allow the Heck coupling to proceed, a base-labile Boc protected N—O bond that is susceptible to cleavage by the naphthoquinone (or its derivatives, or other reagents that cleave the N—O bond used to deblock the 3'-O group), and a (acid-labile protected) primary amine for attachment of the fluorophore. The same linker is therefore used for all four nucleosides.

Figure 9:
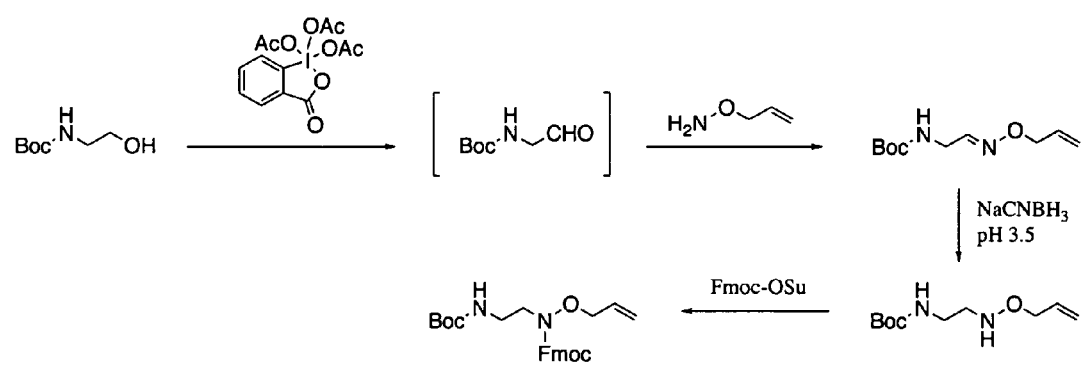
FIG. 9. Synthesis of the linker for attaching the fluorophore to the nucleobases.
Figure 10:
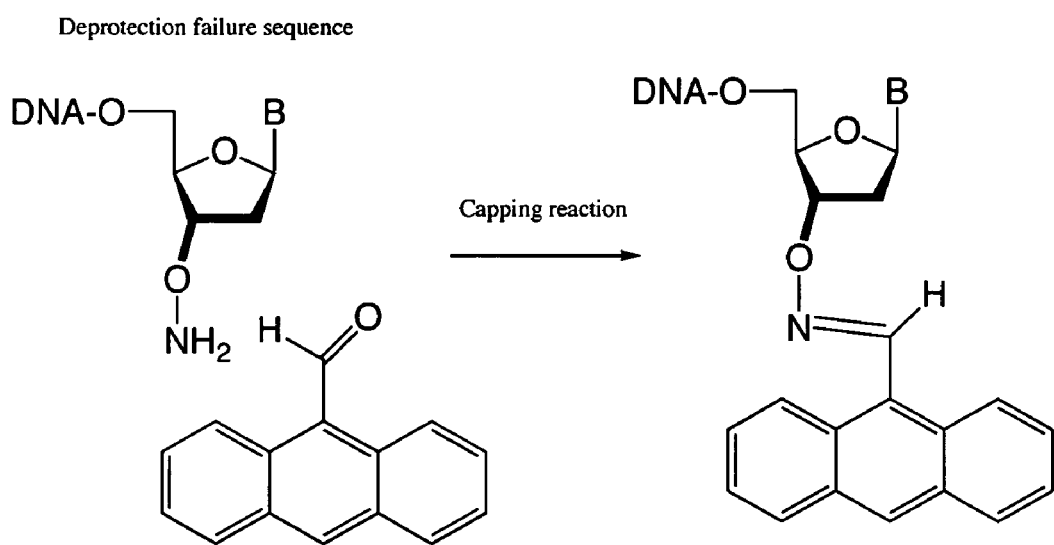
FIG. 10. Capping reaction to append a fluorescent anthracene to a deprotection failure sequence.
Figure 11:
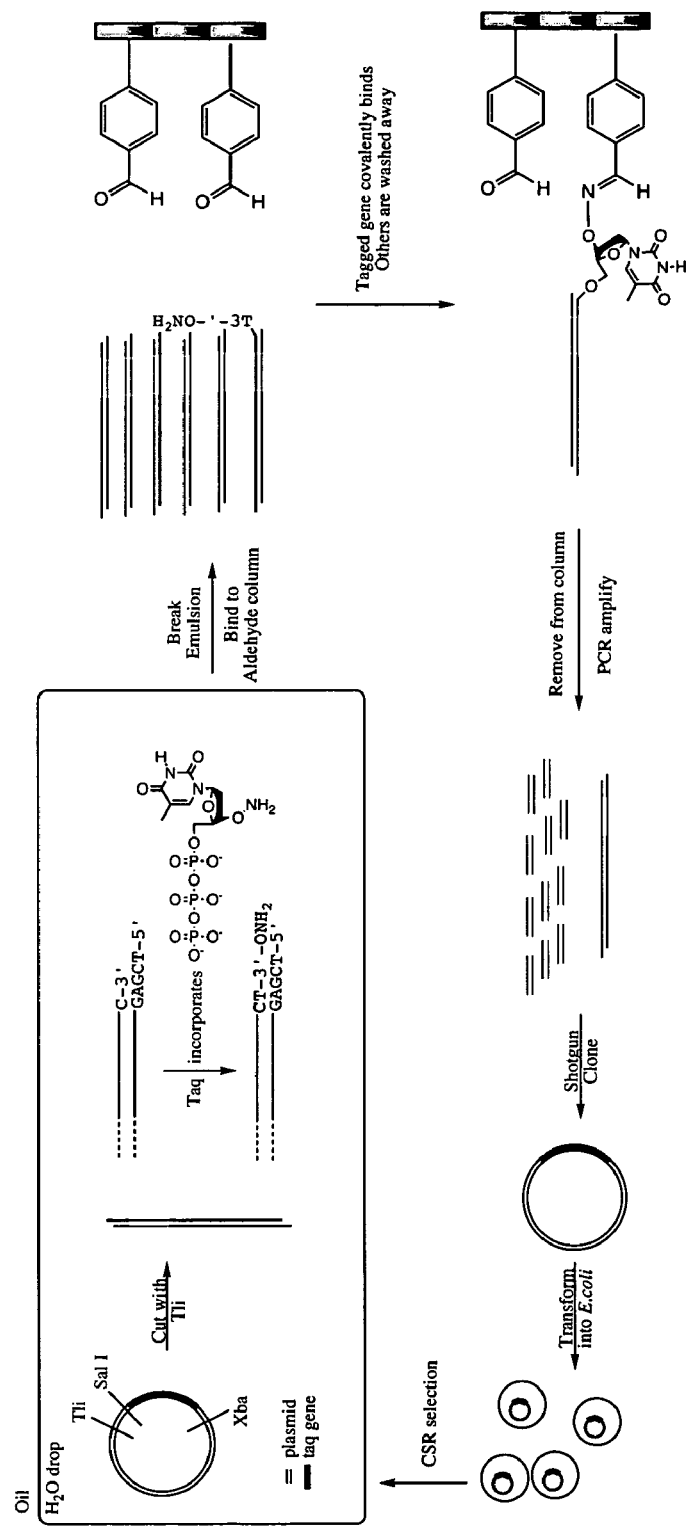
FIG. 11. Scheme for selecting polymerases, after [Gha01].
Figure 12:
FIG. 12. Architecture of hairpin for proof-of-concept for the sequencing-by-synthesis chemistry developed here. The line represents: 5'-Biotin-[12-mer-tail]-[24-mer p53 Val12 hotspot sequence]-[7-mer-spacer]-[10-mer-primer terminating 1 base before the degenerate base position].

The third step is the introduction of the triphosphate group, in analogy to the procedure outlined above. The Boc protection of the linker amine is selectively removed by short treatment with trifluoroacetic acid, reportedly without cleaving either the triphosphate or the glycosidic bond [Sto99]. The attachment of the fluorophore to this amine via an activated ester is a broadly established procedure. Final cleavage of the Fmoc group yields the target compounds. The synthesis of the linker (FIG. 9) starts with Dess-Martin oxidation [Des91] of commercially available Boc-aminoethanol to yield the corresponding aldehyde, which is captured with O-allylhydroxylamine to give the corresponding oxime. Reduction with cyanoborohydride gives the amine which is protected with Fmoc to give the target compound. Several details are described below.

Oxime. tert-Butyl N-(2-hydroxyethyl)carbamate (900 mg; 5.5 mmol) is dissolved in anhydrous dichloromethane (40 mL) at room temperature. Dess-Martin periodinane (2.12 g; 5.0 mmol) is added. The solution is stirred at room temperature for 2 h during which it turned into a milky suspension. Aqueous NaHCO$_3$/Na$_2$S$_2$O$_3$ (sat., 40 mL) is added and the mixture stirred for an additional 30 minutes. The organic phase is separated and the aqueous phase is extracted with dichloromethane (2×50 mL). The combined organic phase is dried with brine (30 mL) and Na$_2$SO$_4$ and concentrated in vacuo, to give a yellow slime. The crude aldehyde is taken up in acetonitrile (30 mL) and THF (20 mL). O-Allylhydroxylamine hydrochloride hydrate (720 mg; ca. 6.5 mmol) and potassium carbonate (900 mg; 6.5 mmol; powdered) are added and the suspension is stirred at room temperature for 30 minutes. The solids are removed by filtration, and the filtrate is concentrated in vacuo. Aqueous work-up (dichloromethane) and flash liquid chromatography (silica; eluent EtOAc/hexanes, 1:4 to 1:2) gives the oxime (expected 670 mg; 63%) as a colorless oil which solidifies at −20° C.

¹H-NMR (CDCl₃; 300 MHz): δ (ppm)=1.45 (s, 9H); 3.89 (t, J=5.0 Hz, 1.2H); 4.01 (t, J=4.9 Hz, 0.8H); 4.53 (dt, J=5.7, 1.4 Hz, 1.2H); 4.58 (dt, J=5.7, 1.4 Hz, 0.8H); 4.94 (br s, 1H); 5.19-5.33 (m, 2H); 5.90-6.04 (m, 1H); 6.74 (t, J=4.3 Hz, 0.4H); 7.44 (t, J=4.8 Hz, 0.6H). ¹³C-NMR (CDCl₃; 75 MHz): δ (ppm)=28.6, 36.8, 40.0, 75.0, 75.3, 80.1, 117.8, 118.2, 134.1, 134.3, 146.8, 149.9, 155.8. HRMS-EI: [MH⁺] calcd for $C_{10}H_{19}O_3N_2$, 215.1396; found, 215.1486.

Amine. The oxime (428 mg; 2 mmol) and methyl orange indicator (ca. 1 mg) are dissolved in methanol (10 mL) at 0° C. A solution of methanolic HCl (6 N aqueous HCl:methanol, 1:1). A solution of sodium cyanoborohydride (150 mg; 2.4 mmol) in methanol (2.4 mL) is slowly added as needed to maintain pH≈3.5 and ice cold temperature. The final solution is stirred at 0° C. and pH 3.5 for an additional 30 minutes. The reaction is quenched by the addition of aq. NaHCO₃ (sat., 5 mL) and aq. NaOH (2 N, 200 µL) and the methanol is removed in vacuo. Aqueous work-up (EtOAc) and flash liquid chromatography (silica; eluent EtOAc/hexanes, 1:2) gives the amine (expected 420 mg; 97%) as a colorless oil. ¹H-NMR (CDCl₃; 300 MHz): a (ppm)=1.45 (s, 9H); 2.99-3.04 (m, 2H); 3.27-3.33 (m, 2H); 4.18 (dt, J=5.9, 1.3 Hz, 2H); 4.97 (br s, 1H); 5.18-5.32 (m, 2H); 5.71 (br s, 1H); 5.86-6.00 (m, 1H). ¹³C-NMR (CDCl₃; 75 MHz): δ (ppm)=28.6, 38.8, 51.7, 75.4, 79.4, 118.2, 134.5, 156.2. HRMS-EI: [MH⁺] calcd for $C_{10}H_{21}O_3N_2$, 217.1552; found, 217.1620.

Final linker. The amine (216 mg; 1 mmol) is added to a solution of sodium carbonate (106 mg; 1 mmol) in water (2.5 mL). Fmoc-OSucc (337 mg; 1 mmol) is dissolved in dioxane (2.5 mL) and added. The mixture is stirred vigorously at room temperature for 2 h. The reaction is quenched by the addition of EtOAc (40 mL) and aq. NaCl (50% sat., 40 mL). Aqueous work-up and flash liquid chromatography (silica; eluent dichloromethane/methanol, 100:0 to 60:1) gives the target compound (expected 130 mg; 30%) as a colorless oil. ¹H-NMR (CDCl₃; 300 MHz): a (ppm)=1.41 (s, 9H); 3.24-3.32 (m, 2H); 3.55-3.60 (m, 2H); 4.22-4.38 (m, 3H); 4.54 (d, J=6.4 Hz, 2H); 4.75 (br s, 1H); 5.22-5.32 (m, 2H); 5.81-5.95 (m, 1H), 7.28-7.43 (m, 4H); 7.60-7.63 (m, 2H); 7.74-7.78 (m, 2H). ¹³C-NMR (CDCl₃; 75 MHz): δ (ppm)=28.6, 38.7, 47.4, 49.8, 67.8, 76.2, 79.6, 120.2, 120.4, 125.2, 127.4, 128.0, 132.3, 141.6, 143.9, 156.0, 157.6. HRMS-EI: [MH⁺] calcd for $C_{25}H_{31}O_5N_2$, 439.2233; found, 439.2244.

Polymerase and Cycle Chemistry Optimization

Reverse transcriptase (RT) and a variety of DNA polymerases of microbial origin are able to incorporate 3'-O-aminonucleoside triphosphates opposite their Watson-Crick pair in a complementary strand acting as a template for primed DNA synthesis. Reverse transcriptase is the ideal polymerase for direct sequencing of messenger RNA. As RT also accepts DNA templates, the enzyme can also be used in the sequencing-by-synthesis architectures being developed that amplify a small number of DNA/RNA molecules to give sequencable DNAs (in polonies, for example). RT as well as other DNA polymerases that accept 3'-O-aminonucleoside triphosphates are also useful for single molecule sequencing by synthesis strategies, if the 3'-O-aminonucleoside triphosphates carry a label that can be visualized at the single molecule level (a fluorescent species such as rhodamine, cy3 and/or cy5, a species that can be visualized by atomic force microscopy, or a species that can be visualized by STEM, for example).

This notwithstanding, it is conceivable that mutant polymerases will be needed to accept to 3'-O-aminonucleoside triphosphates to meet the specifications of specific architectures. To obtain these, polymerases may be mutated, as has been done for other substrate analogs, guided by crystal structures for DNA polymerases and reverse transcriptases [Eom96][LiY98][Kie98][Fra01][Hop99]. These crystal structures show a relatively tight packing between the enzyme and the 3'-hydroxyl group. As with the polymerases engineered to incorporate 2',3'-dideoxy nucleosides, the size of the amino acid residues in contact with the 3'-hydroxyl group is diminished. This disclosure teaches that replacing a phenylalanine in contact with the 3'-OH group by histidine, or a tyrosine in contact with the 3'-OH group by phenylalanine, improves the performance of polymerases for certain assay architectures.

For site directed mutagenesis, the preferred protocol exploits the Stratagene "Quik Change" kit. The process begins with a vector containing the inserted gene between strategically chosen restriction sites. This is transformed into an E. coli strain that is dam⁺. The colonies are grown, picked, and the subsequently extracting the plasmid with a miniprep or phenol-chloroform procedure. The vector is then used as a template for rolling circle replication where the primers bind to the desired mutation site on the gene of interest and introduce the desired mutation. Both primers are designed to contain the desired mutation flanked by 15 nucleotides on each end, and the PCR is cycled for 18 rounds ($t_{denaturation}$:30 sec; $T_{annealing}$: 60 sec.; $T_{extension}$:1 min/kb plasmid) with Pfu Turbo. The reaction is then treated with the DpnI restriction nuclease to degrade the methylated and hemi-methylated DNA of the original plasmid, thus leaving only the mutated DNA produced in the PCR. The nicked product from the rolling circle replication is then transferred into a carrier cell line XL-21 Blue (Stratagene). This method gives an 80% mutation rate, making isolation of the correct variant trivial It is possible that rationally designed mutants of some (or all) of these polymerases may well prove to accept 3'-O-amino-2'-deoxyribonucleoside triphosphates with the high rate and fidelity that meets the specifications for the sequencing-by-synthesis strategy. If this is the case, then work to develop polymerases will be done.

Recognizing that most site-directed mutagenesis is in fact site-directed damage, however, an alternative approach for obtaining polymerases that incorporate 3'-O-amino-2'-deoxyribonucleoside triphosphates to specifications is preferred. This exploits a strategy, called compartmentalized self-replication (CSR), for the evolution of polymerases [Gha01]. In CSR, individual polymerase variants are isolated in water droplets that are suspended in oil. These droplets provide separate compartments into which are put single E. coli cells containing a clone for a single polymerase variants, together with nucleoside triphosphates and other appropriate reagents. Within the drop, each polymerase replicates only its own encoding gene to the exclusion of genes in other compartments. Consequently, only genes encoding active polymerases are manipulated, while inactive variants fail to amplify their own genes and disappear from the gene pool. Among differentially active variants, the more active can be expected to produce proportionally more "offspring," correlating post replication copy number with enzymatic turnover.

As was shown in earlier work by Tawfik and Griffiths [Taw98], the individual drops in a water-in-oil emulsion are stable for prolonged periods at temperatures exceeding 90° C. This approach allows selection for enzymatic activity under a wide range of conditions. Using this approach, Holliger selected for variants of the Taq DNA polymerase with 11-fold higher thermostability than the wild-type enzyme or with a >130-fold increased resistance to the inhibition by heparin [Gha01].

Selection for a polymerase that incorporates 3'-O-amino-2'-deoxynucleotides is done using this system with some minor adaptations. As with Holliger's experiment, the polymerase variants are carried on a pASK75 plasmid. The gene lies after an XbaI site and before a SalI site (C*AATTG) and a TliI site (C*TCGAG) site. The expression of the polymerase variant is done inside the cell. The solution outside the cell, however, contains TliI endonuclease, a thermostable restriction enzyme, as well as a 3'-O-amino-2'-deoxynucleoside triphosphate.

In the first heat cycle, the cell breaks open and the plasmid is delivered to the restriction endonuclease outside the cell. The restriction enzyme cleaves the plasmid at the single TliI site, generating a sticky end with a 3'-overhang that can serve as a polymerization template. The thermostable polymerase variant released from the cell then has the opportunity to add a single 3'-O-amino-2'-deoxynucleotide to the 3'-end of the sticky end in a template-directed fashion.

Polymerases that can do so will tag their own gene with a 3'-ONH$_2$ unit. Work up of the emulsion in ether/water mixtures generates a pool of DNA that encodes variants of Taq. Those variants that were able to add a 3'-O-amino-2'-deoxynucleotide will be tagged with a 3'-ONH$_2$ unit. These will be retained on an aldehyde column through the formation of an oxime. Those that failed to add a 3'-ONH$_2$ unit will be washed from the column, as the only other amine groups in the DNA structure (the exocyclic nucleobase amines) are shielded from reaction by hydrogen bonding interactions and the phosphodiester backbone. Due of the presence of a SalI site between the gene and the 3'-O-amino-2'-deoxynucleotide, the 3'-cap can be cleaved with SalI, the encoding region of the gene can be recovered by cleaving with XbaI. The genes are then shotgun cloned back into the plasmid between the XbaI and SalI sites, ready for another cycle of selection or for analysis.

The TliI site is especially convenient, as it creates a sticky end having one of each of the four nucleotides. If the 3'-O-amino-2'-deoxynucleoside bears a thymine, then termination occurs at the first nucleotide, and one selects for polymerases that incorporate a T-bearing 3'-O-amino-2'-deoxynucleoside opposite A. To select for polymerases that incorporate 3'-O-amino-2'-deoxynucleotides bearing C, we add this triphosphate as well as dTTP. The polymerase will add the first (natural) dA, and then will be challenged to complement the next nucleotide in the template (a G). This process can be completed to screen for polymerases that incorporate all nucleotides.

Conversely, the procedure is reversed to exclude polymerases that incorporate the wrong nucleotide. Thus, the first cycle can include the 3'-O-amino-2'-deoxynucleoside triphosphate carrying a C. A faithful polymerase will not incorporate it opposite the first A in the template. Here, the affinity column cycle is reversed, where the undesired genes are retained on the column, and the desired genes are eluted.

These water-in-oil emulsions are simple to make. Briefly, 0.2 ml of CSR mix [the required 3'-O-amino-2'-deoxynucleoside triphosphate and any required dNTP's (0.2 mM for Taq, 0.8 mM for Vent and 9° N variants), 50 µM tetramethylammonium chloride, and 0.05% (vol/vol) DNase-free pancreatic RNase (Roche) in 1× Taq buffer, as well as the TliI enzyme and induced Taq expresser cells) are added drop wise to 0.4 ml of the organic phase [4.5% (vol/vol) Span 80 (Fluka), 0.4% (vol/vol) Tween 80, and 0.05% (vol/vol) Triton X-100 in light mineral oil (all Sigma)] under constant stirring (1,000 rpm). After addition of the aqueous phase, stirring is continued for 5 minutes more before thermocycling.

Compartment dimensions are determined by light microscopy and by laser diffraction spectroscopy. Compartments had average diameters of 15 µm and proved heat-stable, with no coalescence or changes in compartment size after 20 cycles of PCR as judged by laser diffraction and light microscopy.

For recovering polymerase genes, emulsions are quenched with ether and the phases are separated. The aqueous phase was extracted with ether, and the DNA mixture is passed through an aldehyde affinity column and washed thoroughly. The captured DNA is then removed either by washing with acetone-water mixtures, or by direct cleavage with SalI.

Assembling an Architecture

A working prototype for a sequencing by synthesis is built on a glass slide that uses DNA molecules that are mobilized in the form of a hairpin, and are therefore able to self-prime. The slide is dipped into a solution containing the four 3'-O-amino-2'-deoxynucleoside triphosphates and the polymerase. One fluorescently labeled, capped nucleotide is incorporated on each spot, selected to be the one that is complementary to the next nucleotide on the template. The excess reagents are removed by washing, and a four color fluorescence imager is used to image the surface of the chip. The color of each spot reveals the identity of the nucleotide that was added.

After imaging, any unreacted 3'-OH groups on the self-primed template are capped by adding ddNTPs and DNA polymerase. The 3'-OH cap and the fluorescent label are then removed by adding a solution containing the napthoquinone reagent, and the chip is washed again. The process is repeated.

Figure 13:
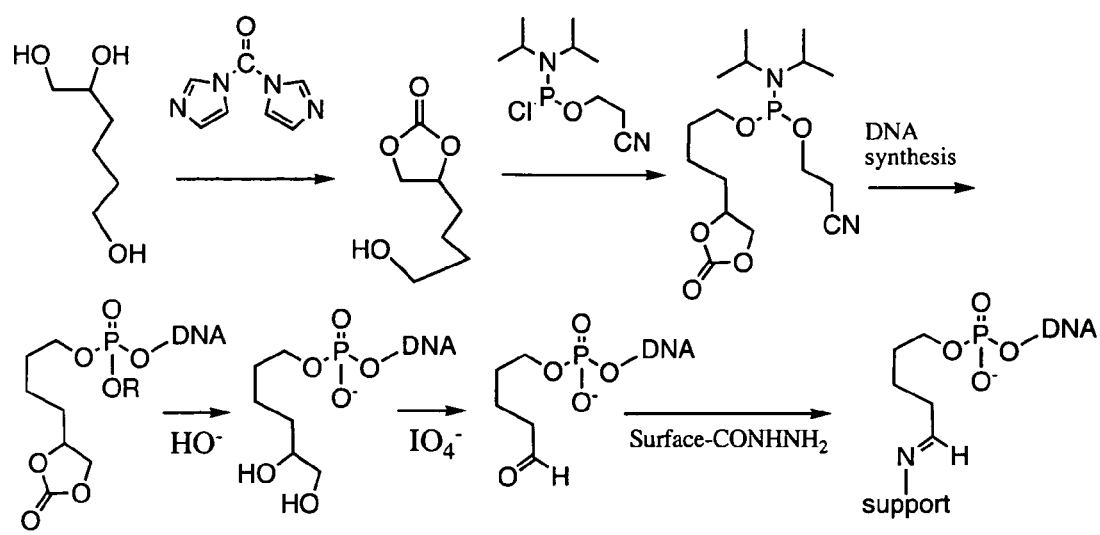
FIG. 13. Immobilization of DNA strands on to the surface of the array

A fluorimeter that is equipped with an accessory to detect fluorescence from a glass slide is used to image the fluorescence emission in our proposed DNA sequencing system. For large scale tests, a multi-color scanning system able to detect four different fluorescent dyes (500 nm-700 nm) (GSI Lumonics ScanArray 5000 Standard Biochip Scanning System) is used. For both proof-of-concept and more advanced work, two-dimensional arrays of hairpin DNA are used. These synthetic templates for evaluating the technique of sequencing by synthesis are immobilized on 96-well plates with well coated with streptavidin. Biotin attachment strategies are preferably replaced by a covalent immobilization chemistry. Such chemistry provides the chip with greater stability and a longer shelf life (FIG. 13).

REFERENCES

[Axe78] Axelrod, V. D., Vartikyan, R. M., Aivazashvili, V. A., Beabealashvili, R. S. (1978) Specific termination of RNA polymerase synthesis as a method of RNA and DNA sequencing. *Nucleic Acids Res.* 5, 3549-3563

[Ber90] Bernofsky, C., Bandara, B. M., Hinojosa, O., Strauss, S. L. (1990) Hypochlorite-modified adenine nucleotides, structure, spin-trapping, and formation by activated guinea pig polymorphonuclear leukocytes. *Free Radic. Res. Commun.* 9, 303-315

[Bit94] Bittner, S., Lempert, D. (1994) Reaction of hydroxylamines with 1,4-quinones. A new direct sythesis of aminoquinones. *Synthesis* 917-919

[Bur94] Burgess, K., Gibbs, R. A., Metzker, M. L., Raghavachari, R. (1994) Synthesis of an oxyamide linked nucleotide dimer and incorporation into antisense oligonucleotide sequences. *J. Chem. Soc. Chem. Commun.* 8, 915-916

[Can95] Canard, B., Cardona, B., Sarfati, R. S. (1995) Catalytic editing properties of DNA polymerases. *Proc. Natl. Acad. Sci. USA* 92, 10859-10863

[Che94] Cheeseman, P. C. (1994) *Method For Sequencing Polynucleotides*, U.S. Pat. No. 5,302,509, issued Apr. 12, 1994

[Chi96] Chiara, J. L., Destabel, C., Gallego, P., Marco-Contelles, J. (1996) Cleavage of N—O bonds promoted by samarium diiodide. Reduction of free or N-acylated O-alkylhydroxylamines. *J. Org. Chem.* 61, 359-360

[Coo94] Cook, P. D., Sanghvi, Y. S. (1994) Preparation of antisense heteroatomic oligonucleotide analogs. PCT nt. Appl. 90 pp

[Cor01] Corsano, A., Chiacchio, U., Pistara, V. (2001) Regeneration of carbonyl compounds from the corresponding oximes. *Synthesis* 1903-1931

[Cor70] Corey, E. J., Richman, J. E. (1970) Reaction of oxime O-acetates with chromous acetate. A method for conversion of ketoximes to ketones under mild conditions. *J. Am. Chem. Soc.*, 92, 5276-5277

[Cor83] Corey E. J., Pyne S. G. (1983) Conversion of ketones having delta, epsilon-pi-functions to cyclopentanols by zinc-trichlorosilane. *Tetrahedron Lett.* 24, 2821-2824

[DeC90] De Clercq, E., Inoue, I., Kondo, K. (1990) Preparation of 3-O-amino-2'-deoxyribonucleoside derivatives as antiviral agents for human retrovirus, particularly human immunodeficiency virus. Eur. Pat. Appl. 14 pp

[Des91] Dess, D. B., Martin, J. C. (1991) A useful 12-I-5 triacetoxyperiodinane (the Dess-Martin periodinane) for the selective oxidation of primary or secondary alcohols and a variety of related 12-I-5 species. *J. Am. Chem. Soc.* 113, 7277-7287

[Dey01] Dey, S., Sheppard, T. L. (2001) Ketone-DNA: A versatile postsynthetic DNA decoration platform. *Org. Lett.* 3, 3983-3986

[Eom96] Eom, S. H., Wang, J. and Steitz, T. A. (1996) Structure of Taq polymerase with DNA at the polymerase active site. *Nature,* 382, 278-281

[Eva00] Evans, S. J., Fogg, M. J., Mamone, A., Davis, M., Pearl, L. H., Connolly, B. A. (2000) Improving dideoxynucleotide-triphosphate utilisation by the hyper-thermophilic DNA polymerase from the archaeon *Pyrococcus furiosus*. *Nucl. Acids Res.* 28, 1059-1066

[Fra01] Franklin, M. C., Wang, J. M. and Steitz, T. A. (2001) Structure of the replicating complex of a Pol alpha family DNA polymerase. *Cell,* 105, 657-667

[Gar99] Gardner, F., Jack, W. E. (1999) Determinants of nucleotide sugar recognition in archaeon DNA polymerase. *Nucl. Acids Res.* 27, 2545-2553

[Gha01] Ghadessy, F. J., Ong, J. L., Holliger, P. (2001) Directed evolution of polymerase function by compartmentalized self-replication. *Proc. Natl. Acad. Sci. USA.* 98, 4552-4557

[Hay71] Hayatsu, H., Pan, S., Ukita, T. (1971) Reaction of sodium hypochlorite with nucleic acids and their constituents. Chem. Pharm. Bull. (Tokyo) 19, 2189-2192

[Hel02] Held, H. A., Benner, S. A. (2002) Challenging artificial genetic systems: Thymidine analogs with 5-position sulfur functionality. *Nucl. Acids Res.* 30, 3857-3869

[Hen04] Hendrickson, C., Devine, K., Benner, S. A. (2004) Probing the necessity of minor groove interactions with three DNA polymerase families using 3-deaza-2'-deoxyadenosine 5'-triphosphate. *Nucl. Acids Res.* 32, 2241-2250

[Hob91] Hobbs, F. W., Cocuzza, A. J. (1991) *Alkynylamino-Nucleotides*. U.S. Pat. No. 5,047,519.

[Hop99] Hopfner, K. P., Eichinger, A., Engh, R. A., et al. (1999) Crystal structure of a thermostable type B DNA polymerase from *Thermococcus gorgonarius*. *Proc. Nat. Acad. Scie USA* 96, 3600-3605.

[Hoy73] Hoyano, Y., Bacon, V., Summons, R. E., Pereira, W. E., Halpern, B., Duffield, A. M. (1973) Chlorination studies, IV. The reaction of aqueous hypochlorous acid with pyrimidine and purine bases. *Biochem. Biophys. Res. Commun.* 53, 1195-1199

[Hym88] Hyman, E. D. (1988) A new method of sequencing DNA. Anal. Biochem. 174, 423-436

[Ima96] Imagawa, K., Hata, E., Yamada, T., et al. (1996) Convenient method for one-pot preparation of 1,2-diamines from nitroolefins. *Chem. Lett.* 4, 291-292

[Ima97] Imagawa, K., Hata, E., Yamada, T., Mukaiyama, T. (1997) A convenient method for the preparation of 1,2-diamines. *Nippon Kagaku Kaishi* 6, 419-424

[Ire86] Ireland, R. E., Varney, M. D. (1986) Approach to the total synthesis of chlorothricolide-synthesis of (+/−)-19, 20-dihydro-24-O-methylchlorothricolide, methyl-ester, ethyl carbonate. *J. Org. Chem.* 51, 635-648

[Ju95] Ju, J., Glazer, A. N., Mathies, P. A. (1996) Cassette labeling for facile construction of energy transfer fluorescent primers. Nucleic Acids Res. 24, 1144-1148

[Ju96] Ju, J., Ruan, C., Fuller, C. W., Glazer, A. N., Mathies, R. A. (1995) Energy transfer fluorescent dye-labeled primers for DNA sequencing and analysis. *Proc. Natl. Acad. Sci. USA* 92, 4347-4351

[Kam99] Kamal, A., Laxman, E., Rao, N. V. (1999) A mild and rapid regeneration of alcohols from their allylic ethers by chlorotrimethylsilane/sodium iodide. *Tetrahedron Lett.* 40, 371-372.

[Kec79] Keck. G. E.; Fleming. S.; Nickeli, D.; Weider. P. (1979) *Synth. Commun.* 9, 281-282.

[Kec95a] Keck, G. E., McHardy, S. F., Murry, J. A. (1995) Total Synthesis of (+)-7-deoxypancratistatin. A radical cyclization approach. *J. Amer. Chem. Soc.* 117, 7289-7290

[Kec95b] Keck, G. E., McHardy, S. F., Wager, T. T. (1995) Reductive cleavage of N—O bonds in hydroxylamine and hydroxanic acid using SmI$_2$/THF. *Tetrahedron Lett.* 36, 7419-7422

[Kec99a] Keck G. E., McHardy S. F., Murry J. A. (1999) Diastereoselective 6-exo radical cyclizations of oxime ethers: Total synthesis of 7-deoxypancaratistatin. *J. Org. Chem.* 64, 4465-4476

[Kec99b] Keck, G. E., Wager, T. T., McHardy, S. F. (1999) Reductive cleavage of N—O bonds in hydroxylamines and hydroxamic acid derivatives using samarium diiodide. *Tetrahedron* 55, 11755-11772

[Khe96] Kheterpal, I., Scherer, J. R., Clark, S. M., Radhakrishnan, A., Ju, J. Y., Ginther, C. L., Sensabaugh, G. F., Mathies, R. A. (1996) DNA sequencing using a four-color confocal fluorescence capillary array scanner. Electrophoresis 17, 1852-1859

[Khl03] Khlestkin, V. K., Mazhukin, D. G. (2003) Recent advances in the application of N,O-dialkylhydroxylamines in organic chemistry. *Curr. Org. Chem.* 7, 967-993

[Khu04] Khurana, J. M., Chauhan, S., Agrawal, A. (2004) Molybdenum in organic synthesis. A review. *Organic Preparations Procedures Int.* 36, 201-276

[Kie98] Kiefer, J. R., Mao, C., Braman, J. C. and Beese, L. S. (1998) Visualizing DNA replication in a catalytically active *Bacillus* DNA polymerase crystal. *Nature* 391, 304-307

[Koc69] Kochetkov, N. K., Budowsky, E. I. (1969) The chemical modification of nucleic acids. *Prog. Nucl. Acid Res. Mol. Biol.* 9, 403-438

[Kon85] Kondo, K., Ogiku, T., Inoue, I. (1985) Synthesis of 5'(3')—O-amino nucleosides. *Symp. Nucleic Acids Chem.* 16, 93-96

[LiY98] Li, Y., Korolev, S. and Waksman, G. (1998) Crystal structures of open and closed forms of binary and ternary complexes of the large fragment of *Thermus aquaticus* DNA polymerase I: structural basis for nucleotide incorporation. *EMBO J.* 17, 7514-7525

[Lud89] Ludwig, J., Eckstein, F. (1989) Rapid and efficient synthesis of nucleoside 5'-o-(1-thiotriphosphates), 5'-triphosphates and 2', 3'-cyclophosphorothioates using 2-chloro-4H-1,3,2-benzodioxaphosphorin-4-one. *J. Org. Chem.* 54, 631-635

[Mah97] Maheswari, V., Balasubramanian, N. (1997) Chemical amplification method for the determination of chromium at trace levels. *Analysis* 25, 2-6

[Mar05] Marradi, M. (2005) Molybdenum hexacarbonyl $Mo(CO)_6$. *SynLett*, 1195-1196

[Mas88] Masoud, N. K., Ishak, M. F. (1988) Kinetics and mechanism of the diazo coupling reaction of arenediazo methyl ethers with beta-naphthol 0.1. the rates of reaction in nonaqueous acid-solutions. *J. Chem. Soc. Perkin* 2, 927-931.

[Mas90] Masoud, N. K. (1990) Kinetics and mechanism of the diazo coupling reaction of arenediazo methyl ethers with β-naphthol. *Bull. Chem. Soc. Ethiopia* 4, 45-55

[Met94] Metzker, M. L., Raghavachari, R., Richards, S., Jacutin, S. E., Civitello, A., Burgess, K., Gibbs, R. A. (1994) Termination of DNA synthesis by novel 3'-modified-deoxyribonucleoside 5'-triphosphates. *Nucleic Acids Res.* 22, 4259-4267

[Mit03] Mitra, R. D., Shendure, J., Olejnik, J., Olejnik, E. K., Church, G. M. (2003) Fluorescent in situ sequencing on polymerase colonies. *Anal. Biochem.* 320, 55-65.

[Mov00] Movassagh, B., Lakouraj, M. M., Ghodrati, K. (2000) Caro's acid supported on silica gel. Part 3: A mild and selective reagent for regeneration of carbonyl compounds from oximes. *Synth. Commun.* 30, 4501-4506

[Nai94] Naito, T., Tajiri, K., Harimoto, T., Ninomiya, I., Kiguchi, T. (1994) Radical cyclizations of oxime ethers connected with aldehydes or ketones. A new entry to cyclic amino-alcohols. *Tetrahedron Lett.* 35, 2205-2206

[Nik00] Nikitin, K. V., Andryukhova, N. P. (2000) Cleavage of the N—O bond in substituted hydroxylamines under basic conditions. *Mendeleev Commun.* 1, 32-33

[Nit85] Nitta, M., Kobayashi, T. (1985) Metal-carbonyl-induced reaction of isoxazoles-ring cleavage and reduction by hexacarbonylmolybdenum, pentacarbonyliron, or nonacarbonyldi-iron. *J. Chem. Soc. Perkin Trans.* 1, 1401-1406

[Oga98] Ogawa, A., Tanaka, M., Sasaki, T., Matsuda, A. (1998) Nucleosides and nucleotides. 180. Synthesis and antitumor activity of nucleosides that have a hydroxylamino group instead of a hydroxyl group at the 2'- or 3'-position of the sugar moiety. *J. Med. Chem.,* 41, 5094-5107

[Pat72] Patton, W., Bacon, V., Duffield, A. M., Halpern, B., Hoyano, Y., Pereira, W., Lederberg, J. (1972) Chlorination studies I. The reaction of aqueous hypochlorous acid with cytosine. *Biochem. Biophys. Res. Commun.* 48, 880-884

[Pat77] Paton, R. Michael; Weber, Rudolf U. (1977) Aryl radical formation during the thermal decomposition of aryldiazo alkyl ethers. *J. Chem. Soc., Chem. Comm.* 769-70

[Ril54] Riley, R. F., Richter, E., Rotheram, M., Todd, N., Myers, L. S., Nusbaum, R. (1954) The hypobromite and hypochlorite oxidation of ammonium hydroxide, hydrazine and hydroxylamine. *J. Am. Chem. Soc.* 76, 3301-3303

[Ron98] Ronaghi, M., Uhlen, M., Nyren, P. (1998) A sequencing method based on real-time pyrophosphate. *Science* 281, 364-365

[Ros00] Roses, A. (2000) Pharmacogenetics and the practice of medicine. *Nature* 405, 857-865

[Roy04] Roychowdhury, A., Illangkoon, H., Hendrickson, C. L., Benner, S. A. (2004) 2'-Deoxycytidines carrying amino and thiol functionality: synthesis and incorporation by vent (exo-) polymerase. *Org. Lett.* 6, 489-492

[Sal98] Salas-Solano, O., Carrilho, E., Kotler, L., Miller, A. W., Goetzinger, W., Sosic, Z., Karger, B. L. (1998) Routine DNA sequencing of 1000 bases in less than one hour by capillary electrophoresis with replaceable linear polyacrylamide solutions. *Anal. Chem.* 70, 3996-4003

[Sek97] Seko, S., Miyake, K. (Sumitomo Chemical), Jpn. Kokai Tokkyo Koho, 1997, JP 09025260

[Sek99] Seko, S., Miyake, K. (1999) Amination of alpha, beta-unsaturated gamma-dicarbonyl compounds with methoxyamines. *Synthetic Commun.* 29, 2487-2492

[Seo04] Seo, T. S., Bai, X., Ruparel, H., Li, Z., Turro, N. J., Ju, J. (2004). Photocleavable fluorescent nucleotides for DNA sequencing on a chip constructed by site-specific coupling chemistry. *Proc. Natl. Acad. Sci. USA* 101, 5488-5493

[Smi86] Smith, L. M., Sanders, J. Z., Kaiser, R. J., Hughes, P., Dodd, C., Connell, C. R., Heiner, C., Kent, S. B. H., Hood, L. E. (1986) Fluorescence detection in automated DNA sequencing analysis. *Nature* 321, 674-679

[Sto99] Stolze, K., Koert, U., Klingel, S., Sagner, G., Wartbichler, R., Engels, J. W. (1999). Synthesis of 3'-sugar- and base-modified nucleotides and their application as potent chain terminators in DNA sequencing. *Helv. Chim. Acta* 82, 1311-1323

[Tab87] Tabor, S., Richardson, C. C. (1987) DNA sequence analysis with a modified bacteriophage T7 DNA polymerase. *Proc. Natl. Acad. Sci. USA* 84, 4767-4771

[Tab95] Tabor, S., Richardson, C. C. (1995) A single residue in DNA polymerases of the *Escherichia coli* DNA polymerase I family is critical for distinguishing between deoxy- and dideoxyribonucleotides. *Proc. Natl. Acad. Sci. USA* 92, 6339-6343

[Taw98] Tawfik, D. S., Griffiths, A. D. (1998) Man-made cell-like compartments for molecular evolution. *Nat Biotechnol* 16, 652-656

[Tim71] Timms, G. H., Wildsmith, E. (1971) The reduction of oximes with tervalent titanium, a mild deoximation procedure and the partial synthesis of erythromycylamine. *Tetrahedron Lett.* 12, 195-198

[Ver91] Verardo, G., Giumanini, A. G., Strazzolini, P. (1991) N-Dealkylation-N-nitrosation of tertiary aromatic amines by n-butyl nitrite. *Tetrahedron* 47, 7845-52

[Wel99] Welch, M. B., Burgess, K. (1999) Synthesis of fluorescent, photolabile 3'-O-protected nucleoside triphosphates for the base addition sequencing scheme. *Nucleosides Nucleotides* 18, 197-201

[Whi97] Whiteman, M., Jenner, A., Halliwell, B. (1997) Hypochlorous acid-induced base modifications in isolated calf thymus DNA. *Chem. Res. Toxicol.* 10, 1240-1246

[Whi99] Whiteman, M., Jenner, A., Halliwell, B. (1999) 8-Chloroadenine, a novel product formed from hypochlorous acid-induced damage to calf thymus DNA. *Biomarkers* 4, 303-310

[You06] Yoo, B. W., Choi, J. W., Yoon, C. M. (2006) A facile and efficient deoxygenation of amine-N-oxides with $Mo(CO)_6$. *Tetrahedron Lett.* 47, 125-126

What is claimed is:

1. A composition of matter having the structure:

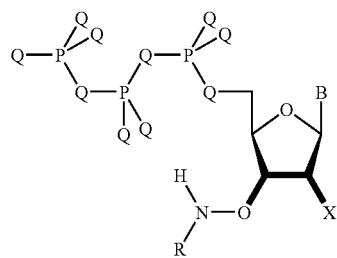

wherein X is selected from the group consisting of H and OH, R is selected from the group consisting of H and CH$_3$, Q is independently selected from the group consisting of O and S, and B is a heterocycle selected from the group consisting of adenine, guanine, thymine, cytosine, uracil, diaminopurine, 7-deazaadenine, 7-deazaaminoadenine, and 7-deazaguanine.

2. The compositions of claim 1, wherein said heterocycle is appended to a linker to which is appended a fluorescent group.

3. A process for extending a DNA primer by template-directed synthesis wherein said process comprises contacting said primer and said template with a DNA polymerase or reverse transcriptase and a 2'-deoxynucleoside triphosphate wherein the 3'-OH group of said triphosphate is blocked by a removable protecting group comprising an —O—N— linkage and having fewer than three non-hydrogen atoms.

4. The process of claim 3 wherein said protecting group is selected from the group consisting of NH$_2$ and NH—CH$_3$.

5. The process of claim 3 wherein said DNA polymerase comprises a mutant DNA polymerase where one of the phenylalanine or tyrosine residues in contact with the 2'-deoxyribose ring is replaced by a histidine or a phenylalanine.

6. A composition of matter having the structure:

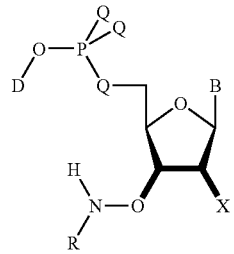

wherein X is selected from the group consisting of H and OH, R is selected from the group consisting of H and CH$_3$, Q is independently selected from the group consisting of O and S, D is a DNA or RNA oligonucleotide, and B is a heterocycle selected from the group consisting of adenine, guanine, thymine, cytosine, uracil, diaminopurine, 7-deazaadenine, 7-deazaaminoadenine, and 7-deazaguanine.

* * * * *